US009459196B2

(12) United States Patent
Zahniser

(10) Patent No.: US 9,459,196 B2
(45) Date of Patent: Oct. 4, 2016

(54) BLOOD ANALYZER CALIBRATION AND ASSESSMENT

(75) Inventor: Russell Zahniser, Dorchester, MA (US)

(73) Assignee: Roche Diagnostics Hematology, Inc., Westborough, MA (US)

( * ) Notice: Subject to any disclaimer, the term of this patent is extended or adjusted under 35 U.S.C. 154(b) by 840 days.

(21) Appl. No.: 13/549,148

(22) Filed: Jul. 13, 2012

(65) Prior Publication Data

US 2013/0024130 A1    Jan. 24, 2013

Related U.S. Application Data

(60) Provisional application No. 61/510,614, filed on Jul. 22, 2011, provisional application No. 61/510,710, filed on Jul. 22, 2011, provisional application No. 61/510,696, filed on Jul. 22, 2011, provisional application No. 61/602,484, filed on Feb. 23, 2012.

(51) Int. Cl.
    *G01N 33/48*    (2006.01)
    *G01N 15/14*    (2006.01)
    *G06F 19/00*    (2011.01)

(52) U.S. Cl.
    CPC ........... *G01N 15/14* (2013.01); *G06F 19/3406* (2013.01)

(58) Field of Classification Search
    CPC .................................................. G06F 19/3406
    USPC .......................................................... 702/20
    See application file for complete search history.

(56) References Cited

U.S. PATENT DOCUMENTS

| | | |
|---|---|---|
| 4,453,266 A | 6/1984 | Bacus |
| 5,287,272 A | 2/1994 | Rutenberg et al. |
| 5,333,207 A | 7/1994 | Rutenberg |
| 5,544,650 A | 8/1996 | Boon et al. |
| 5,655,029 A | 8/1997 | Rutenberg et al. |
| 5,675,760 A | 10/1997 | Houwen et al. |
| 5,740,270 A | 4/1998 | Rutenberg et al. |
| 5,937,364 A | 8/1999 | Westgard et al. |
| 5,939,278 A | 8/1999 | Boon et al. |
| 6,091,842 A | 7/2000 | Domanik et al. |
| 6,148,096 A | 11/2000 | Pressman et al. |
| 6,522,781 B1 | 2/2003 | Norikane et al. |
| 6,748,337 B2 | 6/2004 | Wardlaw et al. |
| 2003/0030783 A1 | 2/2003 | Roche et al. |
| 2006/0050947 A1 | 3/2006 | Petrou et al. |
| 2006/0050948 A1 | 3/2006 | Sumida et al. |
| 2007/0179715 A1 | 8/2007 | Ariyoshi |
| 2007/0217949 A1 | 9/2007 | Mimura et al. |
| 2009/0006003 A1 | 1/2009 | Hirayama et al. |
| 2009/0191585 A1 | 7/2009 | Yamada et al. |
| 2009/0198463 A1 | 8/2009 | Kamihara et al. |
| 2009/0238438 A1 | 9/2009 | Wardlaw et al. |
| 2009/0262993 A1 | 10/2009 | Kotsianti et al. |
| 2009/0323062 A1 | 12/2009 | Ariyoshi et al. |
| 2010/0104169 A1 | 4/2010 | Yamada |
| 2010/0138774 A1 | 6/2010 | Crosbie et al. |
| 2010/0169811 A1 | 7/2010 | Yamada |
| 2010/0183216 A1 | 7/2010 | Yamada |
| 2010/0232675 A1 | 9/2010 | Ortyn et al. |
| 2012/0000268 A1 | 1/2012 | Li et al. |
| 2012/0283975 A1 | 11/2012 | Fukuma |
| 2012/0283980 A1 | 11/2012 | Suga et al. |

FOREIGN PATENT DOCUMENTS

| | | |
|---|---|---|
| CN | 101038293 | 9/2007 |
| CN | 101498735 | 8/2009 |
| CN | 101762584 | 6/2010 |
| CN | 101910842 | 12/2010 |
| DE | 69429481 | 12/2001 |
| EP | 0 549 905 | 7/1993 |
| EP | 0 693 679 | 1/1996 |
| EP | 0 643 360 | 12/2001 |
| EP | 1 998 179 | 12/2008 |
| EP | 2 083 375 | 7/2009 |
| EP | 2 520 933 | 11/2012 |
| JP | 2000-187037 | 7/2000 |
| JP | 2009-180616 | 8/2009 |
| JP | 2010-107257 | 5/2010 |
| JP | 2010-217039 | 9/2010 |
| WO | WO 2009/085534 | 7/2009 |
| WO | WO 2009/135271 | 11/2009 |
| WO | WO 2010/073479 | 7/2010 |

OTHER PUBLICATIONS

"Algorithm" Merriam-Webster (http://www.merriam-webster.com/dictionary/algorithm) last visted Sep. 18, 2015.*
Cambus et al., "A data management software for the Sysmex NE 8000 haematology analyser," *Comput. Biol. Med.* 26(4): 355-359 (1996).
International Search Report and Written Opinion issued in application No. PCT/US2012/046785, mailed Oct. 22, 2012, 15 total pages.
International Search Report and Written Opinion mailed Jan. 3, 2013 issued in international application NO. PCT/US2012/042972, 19 pgs.
Invitation to Pay Additional Fees issued in PCT Application No. PCT/US2012/042972, dated Oct. 11, 2012.
International Preliminary Report on Patentability mailed Jan. 3, 2014 issued in international application No. PCT/US2012/042972, 13 pgs.

(Continued)

*Primary Examiner* — Jerry Lin
(74) *Attorney, Agent, or Firm* — Fish & Richardson P.C.

(57) ABSTRACT

Systems and methods for displaying measured values of a complete blood count ("CBC") parameter include displaying the measured values of the CBC parameter obtained from a plurality of samples from a first lot of a quality control composition, where the displaying includes displaying a marker corresponding to each measured value from the first lot on a plot that includes a two dimensional coordinate system, and where the two dimensional coordinate system includes a first dimension corresponding to a time at which measured values of the CBC parameter were obtained, and a second dimension corresponding to a numerical value of the CBC parameter.

24 Claims, 14 Drawing Sheets

(56) References Cited

OTHER PUBLICATIONS

International Preliminary Report on Patentability mailed Jan. 3, 2014 issued in international application No. PCT/US2012/033636, 8 pgs.
International Search Report and Written Opinion issued in application No. PCT/US2012/033636, mailed Jul. 9, 2012, 15 total pages.
Australian Examination Report No. 1 in Australian Application No. 2012287303, dated Feb. 28, 2014, 4 pages.
Chinese Office Action in Chinese Application No. 201280046475.3, dated Feb. 3, 2015, 12 pages (English Translation).
Wang et al. "Hematology analyzer complete blood count and anemia parameter analysis," *Henan J. of Preventative Medicine*, Dec. 2001, 12(6):1-38.
English Translation of Chinese Office Action issued in related Chinese Application No. 201280029617.5, dated Jul. 21, 2015, 14 pages.
English Translation of Japanese Office Action issued in corresponding JP Application No. 2014-421677 on Apr. 5, 2016, 9 pages.

* cited by examiner

FIG. 5A

BLOOD ANALYZER CALIBRATION AND ASSESSMENT

CROSS-REFERENCE TO RELATED APPLICATIONS

This application claims priority under 35 U.S.C. §119(e) to the following U.S. Provisional Patent Applications: 61/510,614, filed on Jul. 22, 2011; 61/510,710, filed on Jul. 22, 2011; 61/510,696, filed on Jul. 22, 2011; and 61/602,484, filed on Feb. 23, 2012. The entire contents of each of the foregoing applications are incorporated by reference herein.

TECHNICAL FIELD

This disclosure relates to displaying performance data generated from blood analyzers.

BACKGROUND

Ensuring consistency and reproducibility of analysis results from a single automated system, and among multiple systems, are important aspect of automated blood analysis. Control and calibrator compositions are known in the field of hematology for assessing system performance. The following disclosure presents novel methods and systems that permit display and review of a wide variety of performance measurement data from processing of control samples and calibrators by automated laboratory instrumentation including blood analyzers.

SUMMARY

The methods and systems disclosed herein permit display and review of a wide variety of performance measurement data from processing of control samples and calibrators by automated laboratory instrumentation including blood analyzers (also referred to herein as "hematology instruments" or just "instruments"). The data are displayed so that a technician can readily visualize data as well as events and trends in the measurement results (e.g., singular events that affect instrument performance, long-term drift in means, increases in variability). Results are also displayed along a temporal axis to present the technician with information about the frequency with which controls have been analyzed on a particular instrument. Recently measured data from control samples can be displayed together with older data from the same or different samples, or among samples from different lots of control and calibrator compositions, to assess instrument performance over time.

In general, in a first aspect, the disclosure features methods for displaying measured values of a complete blood count ("CBC") parameter, the methods including displaying the measured values of the CBC parameter obtained from a plurality of samples from a first lot of a quality control composition, where the displaying includes displaying a marker corresponding to each measured value from the first lot on a plot featuring a two dimensional coordinate system, and where the two dimensional coordinate system includes a first dimension corresponding to a time at which measured values of the CBC parameter were obtained, and a second dimension corresponding to a numerical value of the CBC parameter.

Embodiments of the methods can include any one or more of the following features.

The markers corresponding to the first lot can each include a coordinate value along the second dimension, where the coordinate value along the second dimension can be calculated based on a difference between the measured value of the CBC parameter associated with the marker and a mean of the measured values of the CBC parameter for the first lot. The coordinate value along the second dimension can be calculated by scaling the difference based on a standard deviation of the measured values of the CBC parameter for the first lot.

The methods can include displaying measured values of the CBC parameter obtained from a plurality of samples from a second lot of a quality control composition, where the displaying includes displaying a marker corresponding to each measured value from the second lot on the plot. The markers corresponding to the second lot can each include a coordinate value along the second dimension, where the coordinate value along the second dimension can be calculated based on a difference between the measured value of the CBC parameter associated with the marker and a mean of the measured values of the CBC parameter for the second lot. The coordinate value along the second dimension for the markers corresponding to the second lot can be calculated by scaling the difference based on a standard deviation of the measured values of the CBC parameter for the second lot.

The methods can include displaying a second set of measured values of a CBC parameter, where the displaying includes displaying a marker corresponding to each of the second set of measured values on a second plot featuring a two dimensional coordinate system, where the two dimensional coordinate system of the second plot includes a first dimension corresponding to a time at which the second set of measured values of the CBC parameter were obtained. The first dimension of the second plot can be identical to the first dimension of the plot of the measured values of the CBC parameter obtained from the first lot. The first dimension of the second plot and the first dimension of the plot of the measured values of the CBC parameter can be identically scaled.

The second set of measured values of the CBC parameter can be obtained from the first lot of samples. The second set of measured values of the CBC parameter can be obtained from a plurality of samples of a second lot of a quality control composition different from the first lot.

The methods can include displaying each of the markers corresponding to each of the first and second lots as user-selectable controls on a user interface. The methods can include, when one of the controls is selected by a user, displaying the value of the CBC parameter associated with the marker. The methods can include, when one of the controls is selected by a user, displaying a mean value and a standard deviation associated with measured values of the lot corresponding to the control adjacent to an axis extending along the second dimension.

The user interface can include a user-selectable control for selecting multiple markers, and the methods can include, when multiple markers are selected by activating the user-selectable control, displaying statistical information about the distribution of measured values of the CBC parameter corresponding to the selected markers. The user interface can include a user-selectable control for displaying the markers corresponding to the second lot, and the methods can include, when the control is de-activated, removing the markers corresponding to the second lot from the plot.

The methods can include, at each of a plurality of different measurement times, determining a mean value of the measured values of the CBC parameter corresponding to the first lot, and displaying a marker on the plot that corresponds to the mean value.

The user interface can include a user-selectable control for reversing a temporal order along the first coordinate, and the methods can include, when the control is activated, displaying each of the markers corresponding to the first lot in an opposite order along a direction corresponding to the first coordinate, and displaying each of the markers corresponding to the second lot in an opposite order along the direction.

Embodiments of the methods can also include any of the other features or steps disclosed herein, in any combination, as appropriate.

In another aspect, the disclosure features methods of displaying complete blood count ("CBC") analysis results obtained from multiple blood analyzers, the methods including displaying a first set of values of at least one CBC parameter for a sample measured using a first blood analyzer on a user interface, and displaying a second set of values of the at least one CBC parameter for the sample measured using a second blood analyzer on the user interface, where the user interface includes a user-selectable control for selecting the first set or the second set, and where the methods further include, when one of the first and second sets of values is selected by activating the control, scaling the other set of values based on the selected set of values.

Embodiments of the methods can include any one or more of the following features.

The first set of values can include a mean value of the at least one CBC parameter measured using the first blood analyzer, and the second set of values can include a mean value of the at least one CBC parameter measured using the second blood analyzer.

Embodiments of the methods can also include any of the other features or steps disclosed herein, in any combination, as appropriate.

In a further aspect, the disclosure features systems for displaying measured values of a complete blood count ("CBC") parameter, the systems including a user interface, and an electronic processor configured to display measured values of the CBC parameter obtained from a plurality of samples from a first lot of a quality control composition, where the displaying includes displaying a marker corresponding to each measured value from the first lot on a plot featuring a two dimensional coordinate system on the user interface, where the two dimensional coordinate system includes a first dimension corresponding to a time at which values of the CBC parameter were obtained, and a second dimension corresponding to a numerical value of the CBC parameter.

Embodiments of the systems can include any one or more of the following features.

The markers corresponding to the first lot can each include a coordinate value along the second dimension, and the electronic processor can be configured to calculate the coordinate value along the second dimension based on a difference between the measured value of the CBC parameter associated with the marker and a mean of the measured values of the CBC parameter for the first lot. The electronic processor can be configured to calculate the coordinate value along the second dimension by scaling the difference based on a standard deviation of the measured values of the CBC parameter for the first lot.

The electronic processor can be configured to display measured values of the CBC parameter obtained from a plurality of samples from a second lot of a quality control composition, where the displaying can include displaying a marker corresponding to each measured value from the second lot on the plot on the user interface. The markers corresponding to the second lot can each include a coordinate value along the second dimension, and the electronic processor can be configured to calculate the coordinate value along the second dimension based on a difference between the measured value of the CBC parameter associated with the marker and a mean of the measured values of the CBC parameter for the second lot. The electronic processor can be configured to calculate the coordinate value along the second dimension for the markers corresponding to the second lot by scaling the difference based on a standard deviation of the measured values of the CBC parameter for the second lot.

The electronic processor can be configured to display a second set of measured values of a CBC parameter, where the displaying includes displaying a marker corresponding to each of the second set of measured values on a second plot on the user interface featuring a two dimensional coordinate system, where the two dimensional coordinate system of the second plot includes a first dimension corresponding to a time at which the second set of measured values of the CBC parameter were obtained. The first dimension of the second plot can be identical to the first dimension of the plot of the measured values of the CBC parameter obtained from the first lot. The first dimension of the second plot and the first dimension of the plot of the measured values of the CBC parameter can be identically scaled.

The second set of measured values of the CBC parameter can be obtained from the first lot of samples. The second set of measured values of the CBC parameter can be obtained from a plurality of samples of a second lot of a quality control composition different from the first lot.

The electronic processor can be configured to display each of the markers corresponding to each of the first and second lots as user-selectable controls on the user interface. The electronic processor can be configured so that, when one of the controls is selected by a user, the electronic processor displays the value of the CBC parameter associated with the marker on the user interface. The electronic processor can be configured so that, when one of the controls is selected by a user, the electronic processor displays a mean value and a standard deviation associated with measured values of the lot corresponding to the control adjacent to an axis extending along the second dimension on the user interface.

The user interface can include a user-selectable control for selecting multiple markers, and the electronic processor can be configured so that, when multiple markers are selected by activating the user-selectable control, the electronic processor displays statistical information about the distribution of measured values of the CBC parameter corresponding to the selected markers on the user interface. The user interface can include a user-selectable control for displaying the markers corresponding to the second lot, and the electronic processor can be configured so that, when the control is de-activated, the electronic processor removes the markers corresponding to the second lot from the plot on the user interface.

The electronic processor can be configured to determine, at each of a plurality of different measurement times, a mean value of the measured values of the CBC parameter corresponding to the first lot, and to display a marker on the plot that corresponds to the mean value on the user interface.

The user interface can include a user-selectable control for reversing a temporal order along the first coordinate, and the electronic processor can be configured so that, when the control is activated, the electronic processor displays each of the markers corresponding to the first lot in an opposite order along a direction corresponding to the first coordinate and displays each of the markers corresponding to the second lot in an opposite order along the direction on the user interface.

Embodiments of the systems can also include any of the other features disclosed herein, in any combination, as appropriate.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

FIGS. 5A-5B are images of a graphical user interface for reporting reproducibility data for an instrument.

Like reference symbols in the various drawings indicate like elements.

DETAILED DESCRIPTION

Figure 1A:
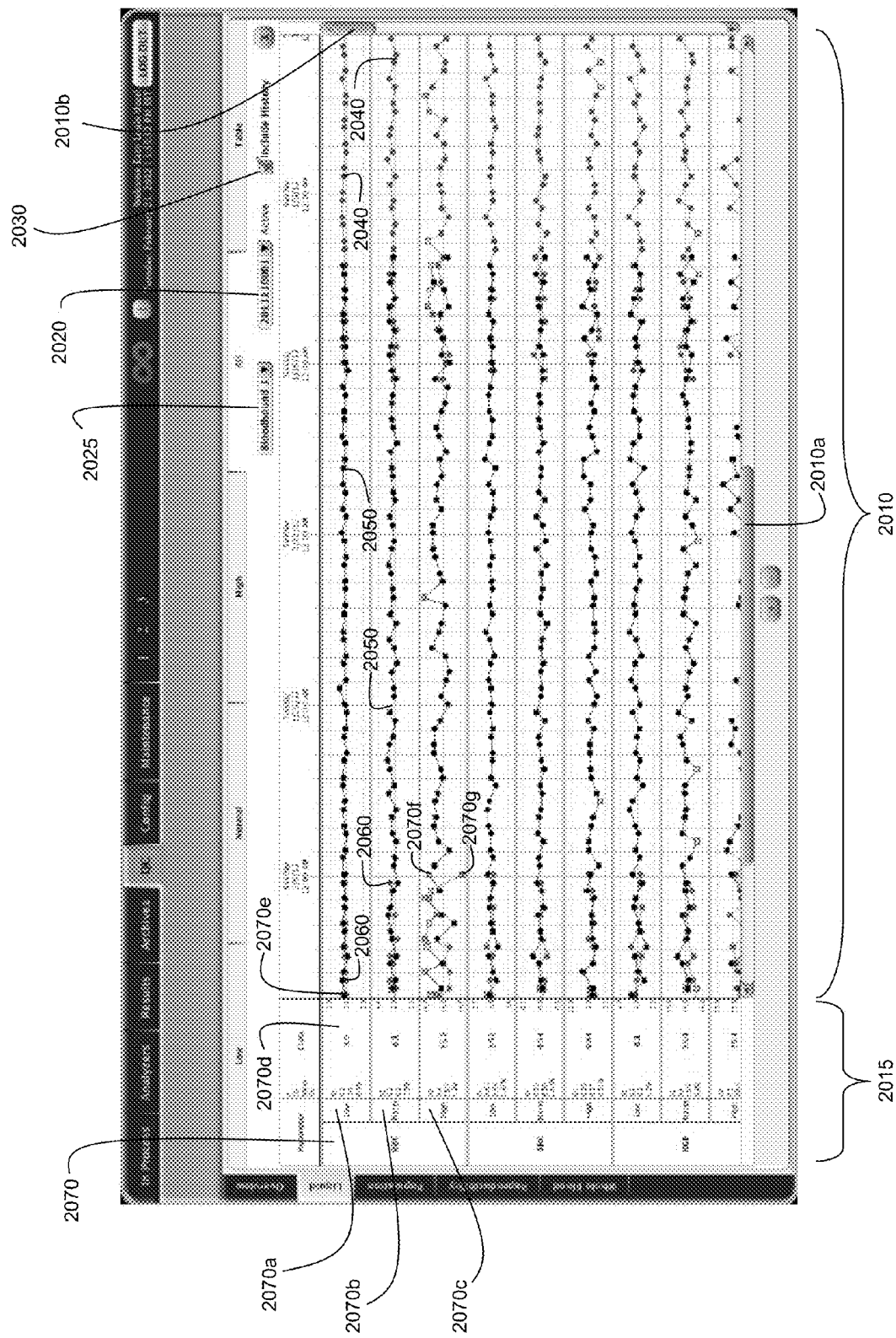
FIG. 1A is an image of a graphical user interface displaying historical quality control data for multiple lots of quality control samples.

A complete blood count (CBC) is a broad screening test that is commonly used to check a patient's general, overall health status. The CBC measures various parameters associated with different blood components. These typically include white blood cell count (e.g., number of white blood cells per unit volume of blood), white blood cell differential (e.g., the numbers of neutrophils, lymphocytes, monocytes, eosinophils, and basophils present in the sample), red blood cell count (e.g., number of red blood cells per unit volume of blood), hemoglobin, hematocrit (e.g., the percentage of red blood cells in a given volume of whole blood), platelet count (e.g., number of platelets per unit volume of blood), mean cell volume (e.g., mean volume of red blood cells), mean cell hemoglobin (e.g., mean amount of hemoglobin per red blood cell), mean cell hemoglobin concentration (e.g., mean concentration of hemoglobin per red blood cell), and red cell distribution width (e.g., variation in size of red blood cells in the sample). CBC results can indicate that a patient is healthy or provide evidence of a variety of disorders, including various infections, anemia, and other physiological conditions. Because determination of a CBC involves multiple measurements, performing a CBC manually is time-consuming and prone to inconsistencies arising from the direct involvement of a technician.

Accordingly, systems and methods have been developed for performing automated CBC measurements. In the subsequent discussion, reference will be made to the analysis of red blood cells by way of example for illustrative purposes. However, it should be understood that the systems and methods disclosed herein can be used to analyze a variety of different blood components, including white blood cells and platelets, as well as the other CBC parameters disclosed herein.

General Considerations

A graphical user interface is used to provide a variety of statistical information and metrics determined by the systems disclosed herein for the sample that is being reviewed. This information can include any of the following associated with red blood cells in a sample:

(a) red blood cell count in the sample (RBC), which can be reported in units of $10^6$/microliter;

(b) hemoglobin concentration in the sample (Hgb), which can be reported in units of g/dL, and which can be calculated from the product of the red blood cell count and the mean cell hemoglobin concentration;

(c) sample hematocrit (Hct), reported as a percentage, which can be calculated from the product of the mean cell volume and the total number of red blood cells divided by the sample volume;

(d) mean cell volume (MCV), which can be reported in units of fL;

(e) mean cell hemoglobin (MCH), which can be reported in units of pg;

(f) mean cell hemoglobin concentration (MCHC), which can be reported in units of g/dL, and which can be calculated as the ratio MCH/MCV and corresponds to the concentration of hemoglobin in red blood cells;

(g) red blood cell distribution width (RDW-CV), which can be reported as a percentage, and which can be calculated from the standard deviation of the distribution of individual red blood cell volumes divided by the mean of the volumes of the individual red blood cells identified and examined in the sample;

(h) red blood cell distribution width (RDW-SD), which can be determined based on a histogram of the distribution of red blood cell volumes in the sample;

(i) nucleated red blood cell count (NRBC), which corresponds to the number of nucleated red blood cells in the sample, and which can be reported in units of $10^3$/microliter;

(j) nucleated red blood cell percentage (NRBC %), which corresponds to the percentage of identified nucleated cells in the sample that are red blood cells;

(k) reticulocyte count (Retic), which corresponds to the number of reticulocytes in the sample, and which can be reported in units of $10^6$/microliter;

(l) reticulocyte cell percentage (Retic %), which corresponds to the percentage of all red blood cells in the same that are identified as reticulocytes; and (m) reticulocyte hemoglobin (RetHE), which corresponds to the hemoglobin concentration in reticulocytes, and which can be reported in units of g/dL.

In addition, the reported information can include information about a platelet count for the sample (PLT, which can be reported in units of $10^3$/microliter), and/or a mean platelet volume measurement (MPV, which can be reported in fL).

The reported information can further include one or more metrics associated with white blood cells in the sample. These metrics include:

(a) white blood cell count (WBC) for the sample, which can be reported in units of $10^3$/microliter;

(b) neutrophil count (NEUT) for the sample which can be reported in units of $10^3$/microliter, and/or percentage of neutrophils (% NEUT) among all white blood cells in the sample;

(c) lymphocyte count (LYMPH) for the sample which can be reported in units of $10^3$/microliter, and/or percentage of lymphocytes (% LYMPH) among all white blood cells in the sample;

(d) monocyte count (MONO) for the sample which can be reported in units of $10^3$/microliter, and/or percentage of monocytes (% MONO) among all white blood cells in the sample;

(e) eosinophil count (EOS) for the sample which can be reported in units of $10^3$/microliter, and/or percentage of eosinophils (% EOS) among all white blood cells in the sample;

(f) basophil count (BASO) for the sample which can be reported in units of $10^3$/microliter, and/or percentage of basophils (% BASO) among all white blood cells in the sample; and (g) unclassified cell count (UC) for the sample which can be reported in units of $10^3$/microliter, and/or percentage of unclassified cells (% UC) among all white blood cells in the sample.

As previously described, the red blood cell, white blood cell, and platelet parameters described above can be measured on a patient sample to form the basis of a CBC. Table 1 shows exemplary upper and lower thresholds for various CBC parameters that can be reported by the system; on the basis of parameters such as these, the technician can determine whether one or more parameters associated with a patient's sample fall outside acceptable ranges, and can use this information to detect or identify disease conditions in the patient.

TABLE 1

| Parameter | Age | Male Lower | Male Upper | Female Lower | Female Upper |
|---|---|---|---|---|---|
| Red Blood Cell Count (RBC) ($10^6$/μL) | 6 mo-2 yr | 3.70 | 5.30 | same | same |
| | 2 yr-6 yr | 3.90 | 5.30 | same | same |
| | 6 yr-12 yr | 4.00 | 5.20 | same | same |
| | 12 yr-18 yr | 4.50 | 5.30 | 4.10 | 5.10 |
| | 18 yr+ | 4.40 | 5.60 | 3.80 | 5.00 |
| Hemoglobin Concentration (Hgb) (g/dL) | 6 mo-2 yr | 10.5 | 13.5 | same | same |
| | 2 yr-6 yr | 11.5 | 13.5 | same | same |
| | 6 yr-12 yr | 11.5 | 15.5 | same | same |
| | 12 yr-18 yr | 13.0 | 15.5 | 12.0 | 15.5 |
| | 18 yr+ | 13.0 | 18.0 | 11.5 | 15.5 |
| Hematocrit (Hct) (%) | 6 mo-2 yr | 33 | 39 | same | same |
| | 2 yr-6 yr | 34 | 40 | same | same |
| | 6 yr-12 yr | 35 | 45 | 35 | 45 |
| | 12 yr-18 yr | 37 | 49 | 36 | 45 |
| | 18 yr+ | 38 | 50 | 36 | 45 |

TABLE 1-continued

| Parameter | Age | Male Lower | Male Upper | Female Lower | Female Upper |
|---|---|---|---|---|---|
| Mean Cell Volume (MCV) (fL) | 6 mo-2 yr | 70 | 86 | same | same |
| | 2 yr-6 yr | 75 | 87 | same | same |
| | 6 yr-12 yr | 77 | 95 | same | same |
| | 12 yr-18 yr | 81 | 98 | same | same |
| | 18 yr+ | 81 | 98 | same | same |
| Mean Cell Hemoglobin (MCH) (pg) | 6 mo-2 yr | 23.0 | 31.0 | same | same |
| | 2 yr-6 yr | 24.0 | 30.0 | same | same |
| | 6 yr-12 yr | 25.0 | 33.0 | same | same |
| | 12 yr-18 yr | 25.0 | 35.0 | same | same |
| | 18 yr+ | 27.3 | 33.6 | same | same |
| Mean Cell Hemoglobin Concentration (MCHC) (g/dL) | 6 mo-2 yr | 30.0 | 36.0 | same | same |
| | 2 yr+ | 32.3 | 35.7 | same | same |
| Platelets (Thrombocytes) ($10^3$/μL) | 0-1 mo | 250 | 450 | same | same |
| | 1 mo-1 yr | 300 | 750 | same | same |
| | 1 yr-3 yr | 250 | 600 | same | same |
| | 3 yr-7 yr | 250 | 550 | same | same |
| | 7 yr-12 yr | 200 | 450 | same | same |
| | 12 yr+ | 150 | 400 | same | same |
| White Blood Cell Count (WBC) ($10^3$/μL) | 6 mo-2 yr | 6.0 | 17.0 | same | same |
| | 2 yr-4 yr | 6.0 | 15.5 | same | same |
| | 4 yr-6 yr | 5.5 | 14.5 | same | same |
| | 6 yr-14 yr | 4.5 | 13.5 | same | same |
| | 14 yr+ | 4.3 | 10.0 | same | same |
| Neutrophil Count (NEUT) ($10^3$/μL) | 6 mo-1 yr | 1.50 | 5.00 | same | same |
| | 1 yr-4 yr | 1.50 | 5.00 | same | same |
| | 4 yr-10 yr | 1.50 | 7.50 | same | same |
| | 10 yr-12 yr | 1.80 | 7.00 | same | same |
| | 12 yr+ | 1.80 | 7.00 | same | same |
| Lymphocyte Count (LYMPH) ($10^3$/μL) | 6 mo-1 yr | 3.00 | 7.00 | same | same |
| | 1 yr-4 yr | 1.50 | 8.50 | same | same |
| | 4 yr-10 yr | 1.50 | 5.00 | same | same |
| | 10 yr-12 yr | 1.20 | 5.00 | same | same |
| | 12 yr+ | 1.00 | 4.80 | same | same |
| Monocyte Count (MONO) ($10^3$/μL) | 6 mo-1 yr | 0 | 0.60 | same | same |
| | 1 yr+ | 0 | 0.80 | same | same |
| Eosinophil Count (EOS) ($10^3$/μL) | 6 mo-1 yr | 0 | 0.80 | same | same |
| | 1 yr+ | 0 | 0.50 | same | same |
| Basophil Count (BASO) ($10^3$/μL) | 6 mo+ | 0 | 0.20 | same | same |

Blood Analyzer Assessment

Ensuring consistency and reproducibility of analysis results from a single automated system, and among multiple systems, is an important aspect of automated blood analysis. Not only is an accurate initial calibration needed to obtain accurate analysis results, but system should remain calibrated (or should be re-calibrated) over time to ensure that analysis results remain consistent and comparable. The systems and methods disclosed herein permit analysis of control samples and calibrators to facilitate comparisons among analyses that occur at different times (e.g., when a lot of control samples is analyzed several times in succession), and to assess mode-to-mode and instrument-to-instrument variability. In particular, the methods and systems disclosed herein include an electronic processor that is configured to calculate and report (e.g., on a display unit) quality control, calibration, reproducibility and performance data to assess the precision and accuracy of an automated blood analyzer. Laboratories typically utilize assayed materials for performing such quality control or calibration measurements, as well as proficiency testing for laboratory personnel using such instruments. These processes involve procedures that measure whole blood parameters such as, for example, one or more parameters determined in a CBC as shown in Table 1 (e.g., a white blood cell ("WBC") differential) and/or one or more of the parameters shown in summary data block 2415 in FIG. 5A (e.g., listed in "Para" column), as will be discussed later.

In general, a calibrator is a prepared sample with known CBC parameter values that is used to calibrate and/or test the accuracy of an instrument. A control sample is a prepared sample with known CBC parameter values that is analyzed on a regular basis to check instrument performance. Control samples and calibrators can be obtained commercially from Streck, Inc. (Omaha, Nebr.), Bio-Rad Laboratories (Hercules, Calif.), or R&D Systems (Minneapolis, Minn.), for example.

Typically, calibrators and control samples include stabilized cell preparations from animal or human whole blood samples. These compositions can be manufactured to contain known levels of different CBC parameters, for example, in separate low-level, normal, and high-level compositions. When handled and tested like a typical patient blood sample, control samples and calibrators provide values for the various parameters of a complete blood count, such as: total red blood cells; hemoglobin; hematocrit; red blood cell indices including mean corpuscular volume, mean corpuscular hemoglobin, and mean corpuscular hemoglobin concentration; red blood cell distribution width; total white blood cells; white blood cell differential counts between various white blood cells including neutrophils, lymphocytes, monocytes, eosinophils, basophils, and immature white blood cells; total platelets; and mean platelet volume. When measured values of these parameters from control samples fall outside of expected ranges, the instrument on which the samples are processed may report erroneous results when analyzing patient samples. Typically, expected ranges of the CBC parameters are smaller for calibrators as compared to control samples.

As used herein, a "lot" refers to a batch of control or calibrator samples. Nominally, each sample in the lot has approximately the same value of each of the CBC parameters, but in practice, the values of each of the CBC parameters vary from sample to sample, so that each lot corresponds to a range of values of each CBC parameter. Typically, the samples in a lot are fabricated so that they have expected values of each of the CBC parameters. By analyzing lots with known CBC parameter ranges on an instrument, the instrument's performance can be verified. A sample(s) from same lot can be re-analyzed at multiple different times to detect variations in the measured values of the CBC parameters, which can provide information about changes in the instrument's performance.

In general, the systems and methods disclosed herein provide for multiple different modes of instrument assessment and calibration. In a first mode, an instrument processes one or more calibrators in the same manner the instrument processes patient blood samples. The results of the processing are used to calibrate the instrument, since values of various CBC parameters are known for the calibrator(s).

In a second mode, one or more control samples are processed by an instrument at intervals to verify instrument performance. The control samples are processed by the instrument in the same manner as a patient blood sample. Because values of various CBC parameters are known for the control samples, the instrument performance can be assessed by comparing measured values of these parameters to the known values of the control samples.

In a third mode, an instrument's reproducibility is assessed. A sample (which can be a blood sample from a patient or a prepared sample) is processed several times in succession (e.g., with no other intervening samples) on an instrument, and the values of various CBC parameters are determined during each processing run. Variability among the values of the measured parameters is assessed to determine the instrument's precision (which is also referred to as its "within-run" precision).

In a fourth mode, a whole blood sample (typically a patient blood sample, but can also be a prepared sample) is processed on different instruments, using different modes on the same or different instruments, or at different times during a defined period such as a day or week. The measured CBC parameters from these processing runs are compared for consistency across multiple instruments, multiple instrument modes, and/or at different times. A comparison of results at different times is referred to as a "patient control" assessment, while comparisons between results from different processing modes are referred to as a "mode to mode" assessment. A comparison between processing results from different instruments is referred to as an "analyzer to analyzer" assessment.

In a fifth mode, population mean values of one or more measured CBC parameters from patient samples are analyzed to determine whether parameter values are "drifting" over time. Parameter values for each sample can be automatically used to recalculate mean values as each sample is processed. This mode of assessment does not rely on calibrators or control samples for assessment, but instead automatically tracks one or more mean values of CBC parameters measured on patient samples over time, for example, during routine processing of patient samples.

As further described below, generation and presentation of performance data associated with the different assessment modes can be optimized for quick and accurate performance assessments of one or more sample processing modes for one or more instruments.

FIG. 1A is an image of a graphical user interface displaying quality control data generated from an automated blood analyzer. The display includes a historical data block 2010 and a summary data block 2015. Historical data block 2010 reports results for either a single lot of quality control compositions, or multiple lots, based on a user-selectable "Include History" overlay feature in control box 2030. Control box 2020 indicates the active quality control composition lot, and contains a drop down menu that can be used to selectively display other lots of quality control samples. Control box 2025 indicates the particular instrument reporting quality control data (e.g., Bloodhound Instrument 1 in FIG. 1A). Quality control data for other instruments can be accessed through a drop down menu within control box 2025.

Summary data block 2015 reports quality control data for each CBC parameter listed in Table 1 measured on the instrument. Data for additional CBC parameters not shown in FIG. 1A, such as additional parameters listed in Table 1 or shown in FIG. 5A (e.g., mean cell volume, hematocrit, mean cell hemoglobin), can be accessed using scroll bar 2010b. As shown in FIG. 1A, summary data block 2015 reports quality control data relating to the system's ability to count white blood cells (WBC) and red blood cells (RBC), and measure hemoglobin content of red blood cells (HGB). Data blocks 2010 and 2015 are advantageously capable of reporting multiple levels of quality control data in a single, integrated display, and are not limited to reporting such data on only a per-level basis per display screen or printed report (which can make direct comparisons among multiple control levels difficult). As an example, referring to FIG. 1A, the WBC count portion of summary data block 2015 contains three discrete subsections for reporting quality control data corresponding to a quality control composition containing a low level of white blood cells (2070a), a quality control composition containing a normal level of white blood cells (2070b), and a quality control composition containing a high level of white blood cells (2070c). By way of example only, these compositions containing low, normal, and high levels of white blood cells can be manufactured to contain expected white blood cell counts of <3.5×10$^9$/L, 7.5 to 9.5×10$^9$/L, and >16.0×10$^9$/L, respectively. More generally, manufactured quality control compositions with a wide variety of expected white blood cells counts (and/or other CBC parameters) can be measured and reported in data blocks 2010 and 2015. Data for quality control compositions corresponding to low, normal, and high values can be reported for other complete blood count parameters such as RBC and HGB as shown in FIG. 1A and/or for any of the additional parameters listed in Table 1.

The display of measurement results for different levels of control samples (e.g., three), each with their own different values of a particular CBC parameter, provides a number of important advantages. Displaying parameter values for multiple levels of controls permits detection of trends such as drift that occur at all control levels simultaneously. Further, displaying parameter values in this manner permits detection of trends such as drift that occur at one control level (e.g., within one range of values of a CBC parameter), but not at others. In addition, such a display provides a multiplex advantage in which the amount of data displayed on a single display screen is increased relative to more conventional displays of results, facilitating more rapid instrument assessment.

More generally, measurement results can be displayed in data block 2010 in parallel for multiple control samples, whether or not the control samples correspond to different ranges of a particular CBC parameter. The control samples can have significantly different values of a CBC parameter, as described above. Alternatively, the control samples can have similar values of a particular CBC parameter. When the control samples have similar values of a particular CBC parameter, differences between the analysis results among the control samples can be used to assess drift among analysis results within the range of values of the CBC parameter that corresponds to the control samples.

In some embodiments, results from analysis of a common control sample analyzed on multiple analysis instruments can be plotted in parallel. Differences among the analysis results can be used to assess variability (e.g., drift) among the instruments over time. If one or more of the instruments are known to be accurately calibrated, departures of the other instruments from an accurately calibrated state can be tracked and readily visualized in display block 2010.

The electronic processor (e.g., the processor associated with the blood analyzer, the processor associated with a viewing station connected to the blood analyzer, or both) can enable display of quality control data using multiple Levey-Jennings plots as shown in data block 2010 of FIG. 1A. Measurement data are plotted as a function of time, shown along the horizontal axis. The vertical axis in each plot is centered about a target mean value and scaled according to a target standard deviation for the measured values (e.g., in Levey-Jennings format). In this manner, significant differences between individual measured values and their associated mean values are comparable on a common scale among different plots or displays. That is, while the absolute numerical values of means, measured values, and displacements from means can differ from one plot to another, a particular measured displacement from a mean value, scaled in units of the standard deviation, is comparable in terms of its rarity among different plots. Further, as shown in FIG. 1A, multiple overlapping lines (e.g., each corresponding to a particular lot), each with its own mean and standard deviation, can be plotted so that all lines are scaled to the same vertical axis.

The display of quality control data shown in FIG. 1A has a number of advantages over more conventional reporting of control data. For example, by plotting measured control values as a function of time on the horizontal axis, a technician can readily visualize not only the sequence in which particular lots were analyzed, but also the time at which lots were analyzed. Thus, a technician can determine whether particular lots were run repeatedly over a single period of analysis (e.g., a cluster of points), or if substantial intervals occurred between the processing of a particular lot (e.g., a gap when a control was not run at an expected time). Further, as explained above, displaying measured values scaled according to standard deviation on the vertical axis facilitates direct comparisons between lots which might be more difficult if parameter values were plotted on a fixed, numeric scale. In particular, lots with different means and/or standard deviations can be readily compared.

When data from different lots of control samples are displayed in parallel (e.g., in historical mode), a technician can readily visualize when two data points occurred in temporal proximity. If the two points correspond to different lots processed at approximately the same time on the same instrument, the data points may be flagged as potentially unreliable.

When the historical overlay mode is enabled for data block 2010 so that analysis results are plotted for a particular CBC parameter across multiple lots, the technician can examine the testing period to ensure that the instrument was maintained under control by an older lot while a new lot was being introduced on the instrument. Further, current and historical lots can be easily compared as if they were part of a single line, and the technician can review the data to examine trends that may be present both in current data and historical data, such as very slow drift and/or a slow increase in variability.

Although the plots shown in data block 2010 provide a number of advantages, other modes of display are also possible. For example, in some embodiments, measured values for only a single parameter level (e.g., "normal" WBC count) are displayed, but the display includes measured values from multiple instruments in parallel. Such a display facilitates direct comparisons between instruments for performance assessment.

In certain embodiments, summary statistics can be displayed for subsets of measured values shown in data block 2010. Summary statistics can include, for example, the number of measured values in the subset, the mean of the measured values, the standard deviation, the coefficient of variation, and/or the percent root-mean-square deviation. Other statistical measures that can be displayed include the minimum and/or maximum measured values within the subset, the range of the values, the median, and the skew.

For example, a technician can select a subset of measured values in one of the plots by clicking and dragging a bounding box around multiple data points in data block 2010. Summary statistics featuring numerical values associated with the selected points are displayed when this selection is complete, for example, in a pop-up window. The technician can, if desired, select a different subset of points and view similar statistical measures for that subset to compare one subset of points with another. For example, the technician can compare summary statistics for the first few data points at the beginning of a line to statistics for the last few data points at the end of a line. Such comparisons can reveal, for example, whether particular statistical measures such as the mean and/or standard deviation are changing over time.

Subsection 2070a of summary data block 2015 includes a summary of reported data for a control sample containing a low-level white blood cell quantity in 2070d. The legends corresponding to each reported data value for the low-level WBC control appear above portion 2070d. The quantity "n" refers to the number of times one or more quality control samples were processed for measuring a particular complete blood count parameter (e.g., 61 quality control measurements for a low-level white blood cell count are reported in portion 2070d). "SD" refers to the standard deviation among the reported measurements for a particular complete blood count parameter (e.g., $0.2 \times 10^3/\mu L$ for quality control measurements of a low-level white blood cell count as reported in portion 2070d). "Mean" refers to the mean or average for all reported measurements for a particular complete blood count parameter (e.g., $3.4 \times 10^3$ white blood cells per microliter of a quality control composition containing a low level of white blood cells as reported in portion 2070D based on 61 measurements of a white blood cell count). "CV" refers to the coefficient of variation for the reported measurements for a particular complete blood count parameter (e.g., 4.4% for quality control measurements of a low-level white blood cell count as reported in portion 2070d). As shown in FIG. 1A, the "n," "SD," "Mean," and "CV" values are reported for multiple complete blood count parameters (e.g., RBC or HGB shown in summary data block 2015) and for multiple levels for each parameter (e.g., low, normal, and high level RBC counts shown in summary data block 2015).

Quality control data are reported across multiple samples or multiple lots of quality control compositions as shown in FIG. 1A, in contrast to conventional quality control data reporting tools and hematology instruments. Such conventional tools and instruments typically present data for only a single lot or sample of a quality control composition without any ability to make lot-to-lot or sample-to-sample comparisons; single-lot or single-sample reporting, in turn, limits the ability of laboratory technicians to view trends in quality control data to only the specific lot or sample reported. The systems described herein advantageously can report quality control data for multiple lots or samples of quality control material, e.g., in historical overlay fashion. This improves a technician's ability to observe and monitor trends in instrument performance and, in particular, to assess whether out-of-range quality control data relate to a problem specific to a given quality control material lot or sample, or indicate that the instrument is not functioning properly or requires maintenance. Further, one-time events that may affect multiple levels of controls can be detected using the methods and systems disclosed herein. For example, a technician can observe that within a short time period, multiple levels of controls have significantly higher measured parameter values than the control sample expected values, which may indicate a temporary event affecting an instrument at a particular point in time. As another example, the technician can observe that at approximately the same time, values of a measured parameter for multiple levels of controls were "stepped up" or "stepped down" (e.g., systematically shifted higher or lower), indicating a one-time event that affected the instrument performance.

Referring to FIG. 1A and by way of example, quality control data for three different lots of a quality control composition containing a low level of white blood cells are reported in a Levey-Jennings plot adjacent to portion 2070d of the summary data block 2015. White blood cell count data for each of three different lots of the quality control composition, 2040, 2050, and 2060 are shown in data block 2010 of FIG. 1A. Colors or other display conventions may be used to distinguish among data corresponding to the various quality control lots reported in data block 2010. Each dot within portions 2040, 2050, and 2060 of the plot represents a single test at a given time for a particular parameter of the quality control composition. For example, the times of each of the tests in the upper plot labeled 2040 for the low-level white blood cell count plot can be readily determined from the horizontal axis in the plot, which is displayed across the top of data block 2010. In general, older quality control data appear on the right-hand portion of data block 2010 while newer quality control data appear on the left-hand portion of data block 2010 as shown in FIG. 1A. As additional quality control samples are processed, new quality control data populate the left-most portions of the plots shown in display block 2010, thereby shifting historical data to the right of data block 2010. A scroll bar 2010a can be used to view quality control data for specific time periods. In addition, the "+" and "−" buttons at the bottom of data block 2010 can be used to increase or decrease the time scale for the data plots.

Control box 2020 indicates the active lot of a quality control composition for data reporting. Based on user-defined criteria, a lot becomes active after a suitable number of quality control tests have been performed to generate a reliable mean, standard deviation, and/or coefficient of variation values for parameters (e.g., CBC parameters) assessed using the lot. For example, a given laboratory may require at least 10 tests, 20 tests, 30 tests or more for any given lot of a quality control composition before relying upon the mean, standard deviation, and coefficient of variation to assess new quality control tests using the lot. For example, in FIG. 1A, the lot labeled 2050 identifies the active lot of quality control material as indicated in control box 2020. As shown in FIG. 1A, lot 2060 can indicate quality control data for a new lot of quality control material where additional testing is required before this lot can be used to perform new quality control tests.

Different display formats can be used to indicate whether quality control data fall within acceptable ranges, approach thresholds defining the acceptable ranges, or fall outside of acceptable ranges. For example, reported data falling within an acceptable range for a given CBC parameter can be plotted using solid, single-color, circular points. As shown in FIG. 1A, all reported data for assessing the instrument's ability to accurately count a low level of white blood cells in multiple lots of quality control compositions fall within acceptable ranges as noted by the format of lots 2040, 2050, and 2060 of the plot. The upper and lower limits of this acceptable range are indicated in portion 2070d of summary data block 2015, and by the corresponding dotted line portions of the plot: $3.9 \times 10^3$ white blood cells per microliter and $3.0 \times 10^3$ white blood cells per microliter. The central value within portion 2070d (i.e., $3.5 \times 10^3$ white blood cells per microliter) represents the selected quality control data point 2070e of the plot, as noted by the box surrounding the data point. As the user selects different points within the plot, for example, by pointing and clicking with a mouse, the central value of portion 2070d changes to reflect the selected data point. Also, the user can exclude (e.g., by de-selecting) one or more specific data points within the plot such that data from the excluded point(s) are not included within the data set used to report n, SD, mean, and CV for the given complete blood count parameter.

Continuing with the example, quality control data for control samples with a high white blood cell count appear in portion 2070c of summary data block 2015 and the Levey-Jennings plot associated with portion 2070c of FIG. 1A. The quality control data plot for assessing a high level of white blood cells contains two points in FIG. 1A labeled 2070f and 2070g. The format of data point 2070f indicates that this particular test for a high level white blood cell control is approaching the upper limit of the acceptable range of reported values for the white blood cell parameter. This user-defined feature can be set to alert the user that the reported data is approaching the upper or lower threshold of an acceptable range of quality control data, for example, if the reported result is within one standard deviation unit from the outer limit of the acceptable range or if the reported result is two standard deviation units beyond the mean of the measured values. In certain embodiments, other display formats and colors can be used to set the warning indicator represented by point 2070f. Data point 2070g indicates that the particular measurement of a high white blood cell count falls outside of the acceptable range, for example, by three or more standard deviation units (e.g., as recommended by the Clinical and Laboratory Standards Institute or other laboratory standards-setting or accrediting bodies known in the art). In other embodiments, other display formats and colors can be used to indicate that a particular quality control measurement falls outside of an acceptable range.

In general, measured values can be displayed in data block 2010 using a variety of colors and other formats to indicate instrument status. For example, a particular point can be colored according to various status identifiers (e.g., "good," "warning," "failure," and "excluded"). Points that are excluded can be detached from the plot line connecting the measured data points to indicate their status in the display block. In some embodiments, when a technician manipulates a pointing device (e.g., a mouse cursor) so that it hovers over a measured value that has been assigned "failure" status, the interface can display a dynamically-generated message (e.g., a tooltip) stating the reason for the failure.

Figure 1B:
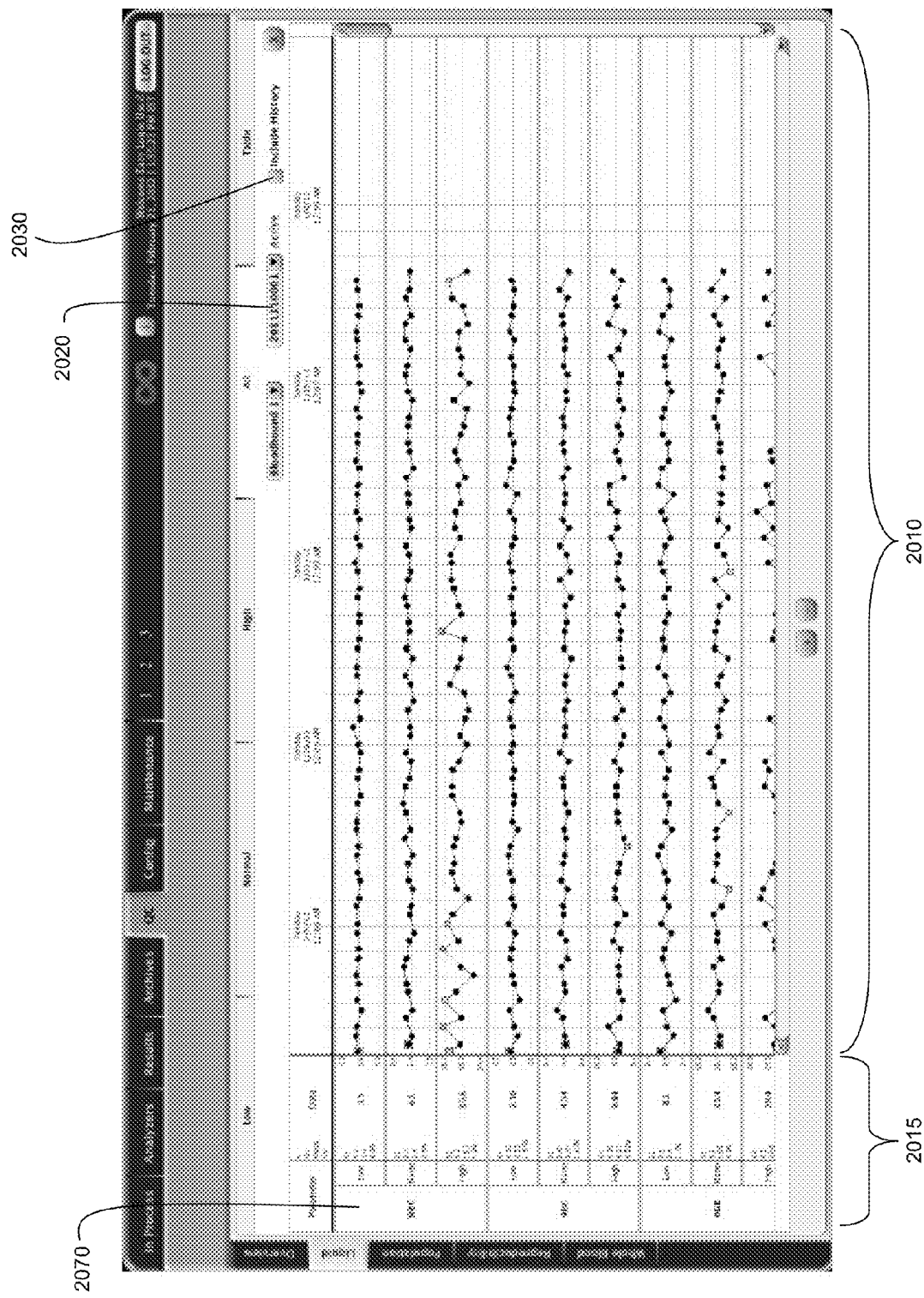
FIGS. 1B-1D are images of a graphical user interface displaying quality control data for one lot of quality control material.
Figure 1C:
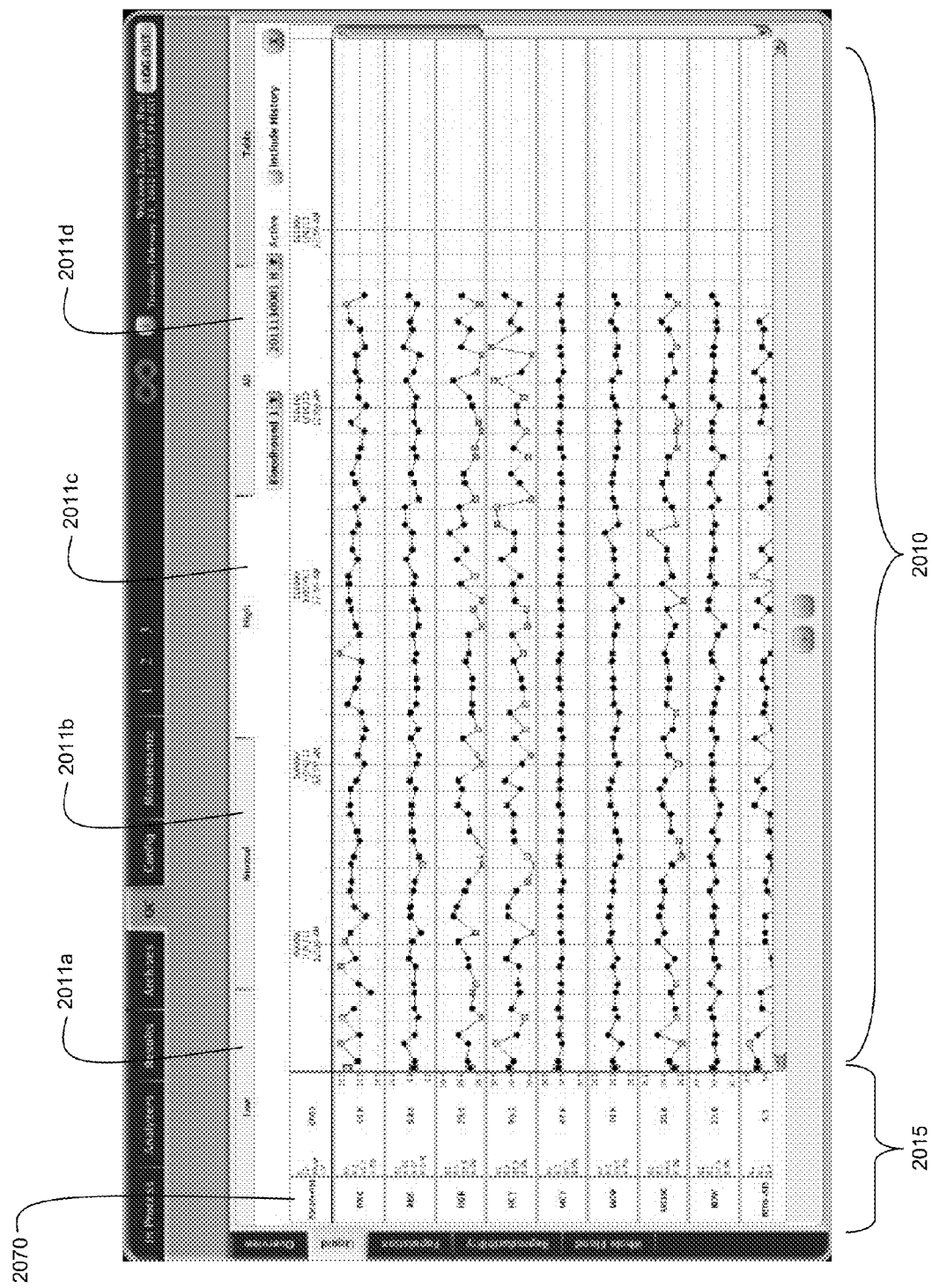
Figure 1D:
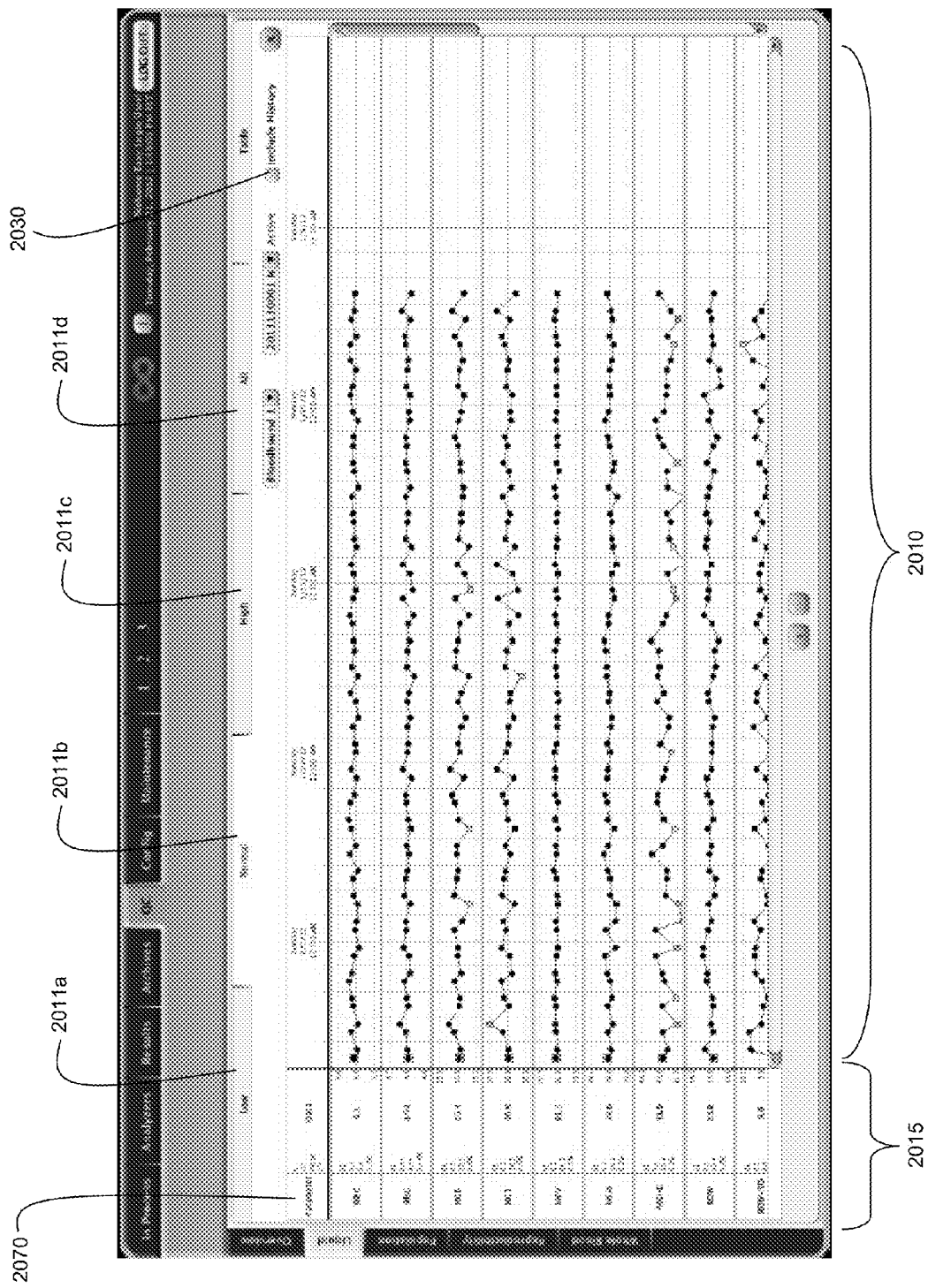

FIGS. 1B-1D show user interface displays containing quality control data for an active quality control lot reported in a similar manner as shown in FIG. 1A, but without the history overlay function (e.g., control 2030) selected. FIG. 1B shows quality control data for low, normal, and high-level quality control compositions of a given lot (No. 2011110001 indicated in box 2020). CBC parameters measured on a lot of high-level quality control materials are reported in the interface shown in FIG. 1C under the "High" tab control 2010c. In FIG. 1C, CBC parameters measured on a lot of normal-level quality control materials are reported under the "Normal" tab 2010b. The tabs low, normal, high, and all (labeled 2010a, 2010b, 2010c, and 2010d in FIG. 1D, respectively) allow a user to quickly access quality control data for certain levels or all levels of quality control samples processed on the instrument.

Embodiments of the graphical user interfaces disclosed herein can also include a variety of additional features to facilitate display of measured parameter values and assessment of instrument performance. In some embodiments, selecting a particular lot changes the plot associated with the lot so that measured values for the selected lot are plotted on a numeric scale on the vertical axis of the plot. As discussed above, control box 2020 can be used to select the active lot. Alternatively, or in addition, the active lot can be selected (and the display in control box 2020 updated) by clicking on a plotted data point within a particular lot to "select" the lot.

When a particular lot is selected, statistical values associated with the lot (e.g., standard deviation SD, coefficient of variance CV, and number of measurements of the sample n) can be displayed in a popup display box or in a summary area of the interface.

In certain embodiments, the interface includes a control that, when activated, allows a technician to zoom the display out or in along the horizontal axis. This permits viewing of a subset of plotted measured values, for example, or the entire range of measured values for any of the lots. The display can be scaled simultaneously for all plots, or individually for any of the plots.

In some embodiments, the interface includes a control that, when activated, permits a technician to toggle the historical display of data on and off. For example, selecting the historical display box 2030 in FIG. 1A displays historical quality control data. By turning off the historical display, for example as shown in FIGS. 1B-1D, the technician can view data from a single lot. The interface can also include a review control (e.g., a scroll bar such as scroll bar 2010a in FIG. 1A) that allows a technician to review older data by moving backwards through the historical display of data. When the historical display is toggled off, the review control can be locked to a range that coincides with the selected lot so that the technician does not move backward in time beyond the first historical data point for the selected lot as shown in FIGS. 1B-1D.

In certain embodiments, the interface includes a control that, when activated, permits a technician to select the side of the plot on which new measured values are displayed. For example, as shown in FIG. 1A, new points can be displayed on the left-hand side of the plot, with the vertical axis and summary information (e.g., data block 2015) also on the left-hand side. By activating the control, the technician can switch any of the plots (or all of the plots) so that new data points are displayed on the right-hand side, and the vertical axis and summary information also appear on the right-hand side.

In some embodiments, the interface includes a control that, when activated, displays measurement results from other instruments for the lot that is currently selected. For example, control box 2025 in FIG. 1A can be used to select other instruments for quality control data reporting in data block 2010 and summary data block 2015. The measurement results from other instruments can be displayed along a common range of horizontal axis values (e.g., over a common time interval). The common time interval can be the interval displayed for the selected lot.

Figure 2:
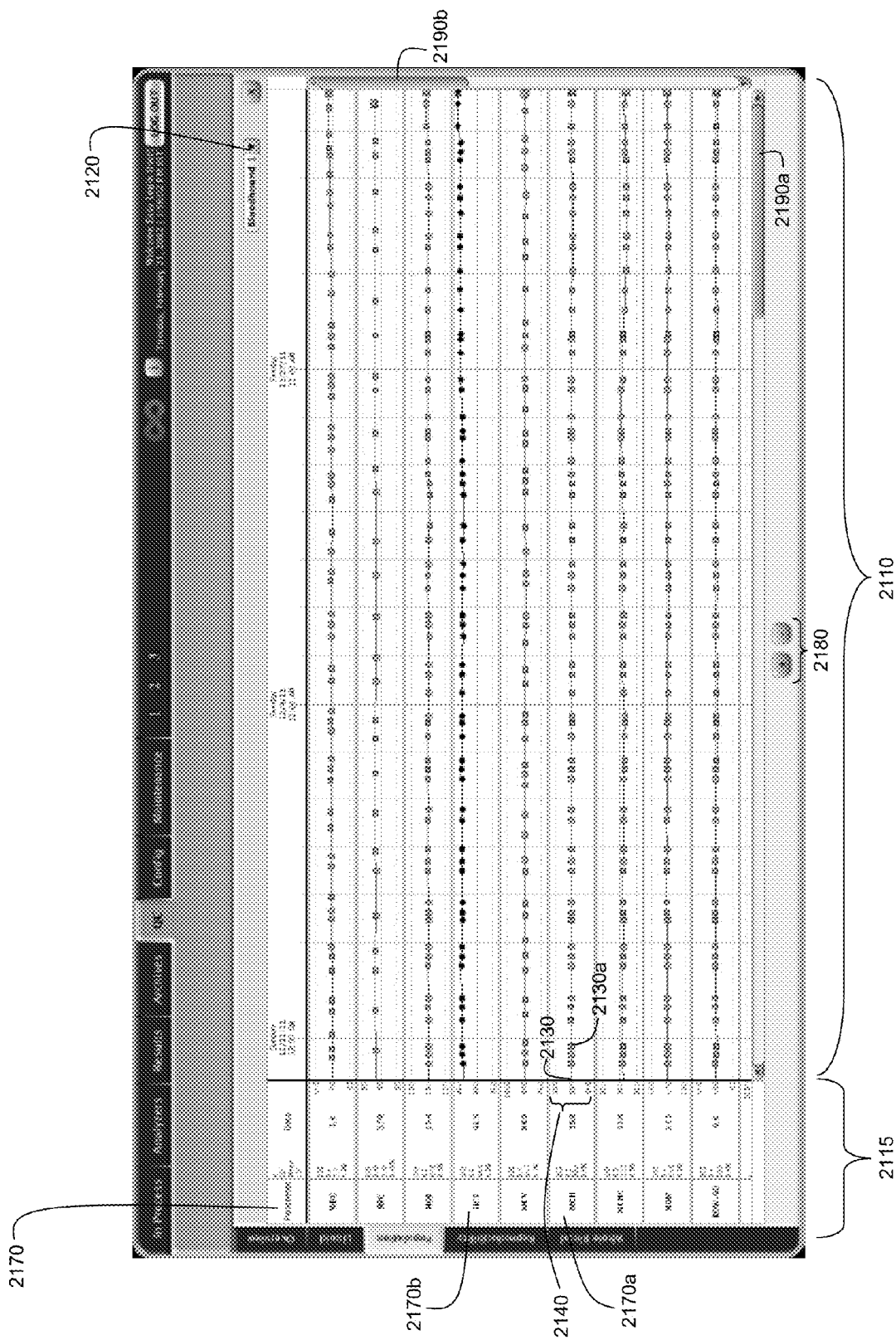
FIG. 2 is an image of a graphical user interface for monitoring trends in instrument performance.

In some embodiments, the graphical user interfaces disclosed herein display certain patient sample data to report and monitor trends in instrument performance over time. FIG. 2 shows historical trends for all CBC parameters measured on a particular instrument (Instrument Bloodhound 1) over time. For example, these monitored CBC parameters can include the identified parameters in the "Parameter" column 2170 of summary data block 2115. Additional CBC parameters can be accessed through scroll bar 2190b. For a given CBC parameter, such as mean cell hemoglobin (MCH), portions of data block 2110 enable the user to assess the instrument's ability to measure a MCH value for red blood cells in patient samples (e.g., 2140 and 2170a). Plot 2130, as further described below, reports MCH data in relation to a mean MCH value for multiple patient samples measured over time. For example, plot 2130 for measured MCH values is shown in relation to a mean MCH value of 30.1 picograms/cell calculated from a total of 263 data sets as noted in box 2140. The plot contains upper and lower limits of an acceptable range of MCH values noted by the dotted lines parallel to plot 2130. By collecting and reporting patient sample data over time as the instrument processes patient samples, users can easily monitor instrument performance and, for example, recognize instrument "drift," where a reported CBC parameter, over time, approaches and then exceeds the limit of an acceptable performance range.

Instrument users can configure the criteria to select and display sample data for monitoring instrument performance trends. For example, each data point of the CBC parameter plots shown in FIG. 2 can represent a single patient sample or the mean of multiple patient samples processed at a particular point in time. For example, point 2130a may represent the mean of MCH values measured on 10, 20, 30 or more patient samples around 12:00 am Sunday, Dec. 11, 2011. Thus each point can correspond to user-defined criteria (e.g., a random number of samples processed on a given day, such as 20). In addition, the user can exclude abnormally high or low results from the reported trend analysis data. For example, the user can configure the reporting tool to exclude CBC parameter results from exceptional cases or samples obtained from critically ill patients. Where each plotted data point corresponds to multiple patient samples, a user can double-click on the point to further review individual test measurements and/or exclude one or more individual test measurements from the reporting function. As with reported quality control data discussed in connection with FIG. 1A, different display formats can be used to indicate whether the data falls within an acceptable range, approaches the upper or lower threshold of an acceptable range, or falls outside of an acceptable range based (e.g., based on standard deviation units relative to the reported mean).

In some embodiments, a graphical user interface for displaying sample data can be configured to compare samples processed using multiple operating modes for a particular instrument, using a single operating mode on multiple instruments, or using multiple operating modes for multiple instruments. A blood analyzer can have multiple sample processing modes corresponding to different sampling paths. An open or normal mode typically refers to routine sample processing, for example, from a sample tube rack conveyor mechanism within the automated instrument. Higher priority ("stat") samples can bypass the sample tube rack conveyor mechanism used for open or normal mode processing through a stat drawer or priority drawer when processed in a stat or priority processing mode. Further, in an open port mode where the instrument contains an open mode port aspirator, patient samples can be manually aspirated from a sample tube for further processing. Further details of normal, stat, and open mode sample processing, including exemplary instrument components utilized in sample processing during each operating mode, are further described in co-pending U.S. Provisional Patent Application No. 61/510,700 filed on Jul. 22, 2011, the entire contents of which are incorporated herein by reference.

Each of these different processing modes corresponds to a different sampling path. As such, variability in the processing of samples can arise from differences in the sampling paths. The interfaces disclosed herein permit measurement, reporting, and comparison of processing results (e.g., various CBC parameters) for the same sample processed in different modes (e.g., normal, stat, and open) to determine whether such variations exist, and to correct for them if needed.

Figure 3A:
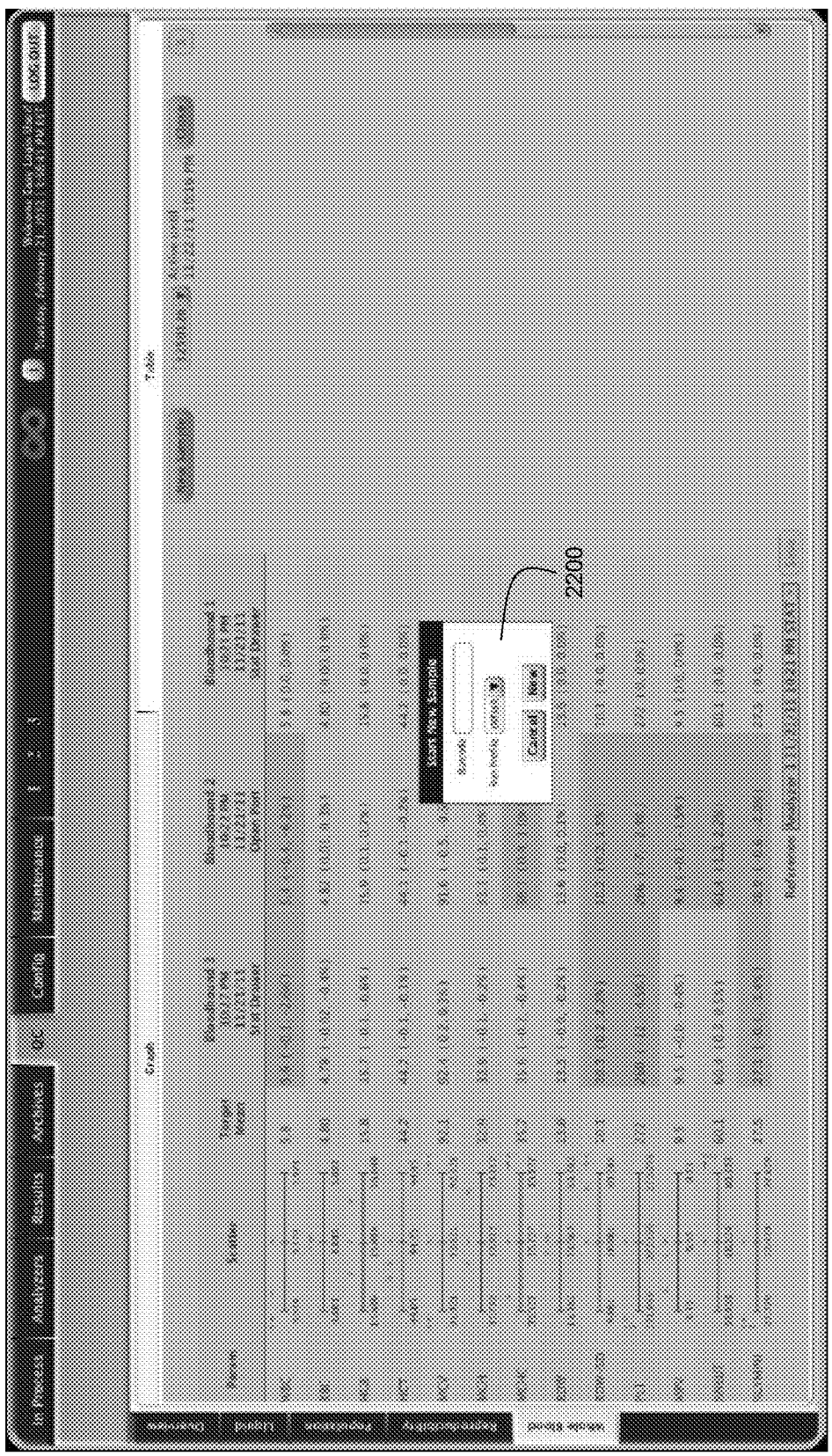
FIGS. 3A-3B are images of a graphical user interface for reporting mode-to-mode comparison data generated on one or more instruments.

FIG. 3A shows a control box 2200 on the graphical user interface of display unit 110, which prompts the user to identify a particular sample for mode-to-mode comparisons across multiple instruments. A bar code number or other identifying information associated with a particular blood sample tube can be entered through the prompt thereby alerting the instrument that a given patient sample, control lot, control sample, or calibrator will be processed for mode-to-mode comparisions. Control box 2200 can also be used to initiate the instrument performance assessment through a dedicated button labeled "New" in FIG. 3A or other appropriate identifier. The instrument(s) associated with the performance assessment then processes the patient sample in the processing mode(s) under evaluation.

Figure 3B:
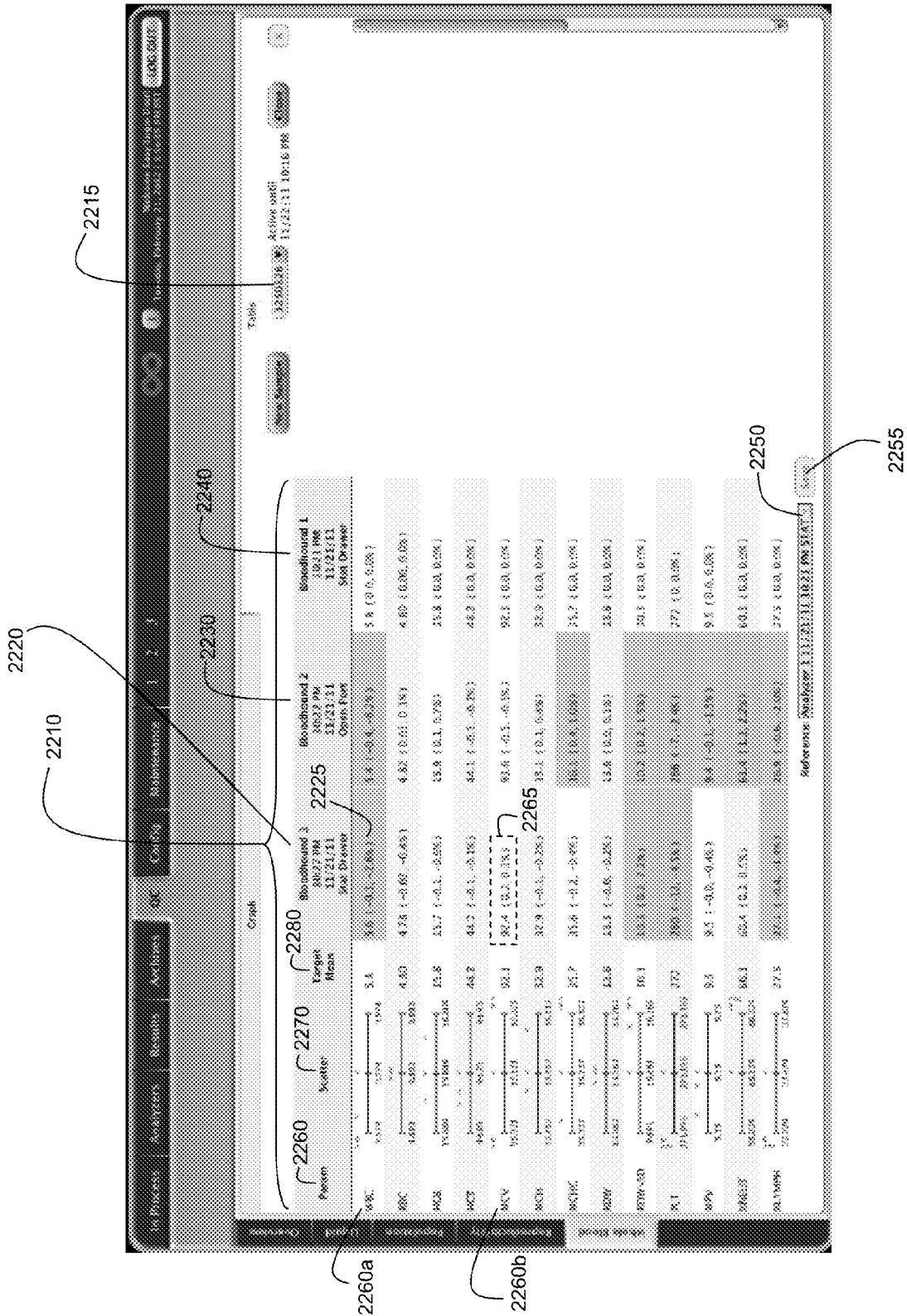

FIG. 3B contains a data block 2010 reporting CBC parameters for a given patient sample identified in control box 2215. Three separate hematology instruments processed this patient sample (i.e., sample identifier No. 3250126) are shown in FIG. 3B. The three instruments are identified as "Bloodhound Instrument 1," "Bloodhound Instrument 2," and "Bloodhound Instrument 3" and listed at the top of columns 2240, 2230, and 2220, respectively. Bloodhound Instruments 1 and 3 processed the sample in stat processing mode (noted as "Stat Drawer" in columns 2240 and 2220, respectively). Bloodhound Instrument 2 processed the sample in open port mode as indicated at the top of column 2230. Data for the various CBC parameters are reported for each instrument and processing mode evaluated in the comparison. For example and as shown in row 2260a, the white blood cell count or WBC parameter is reported as $5.6\times10^3$ cells/microliter of blood, $5.4\times10^3$ cells/microliter of blood, and $5.8\times10^3$ cells/microliter of blood, respectively, for the sample processed on Bloodhound Instrument 3 (Stat Mode), Bloodhound Instrument 2 (Open Mode), and Bloodhound Instrument 1 (Stat Mode). Other CBC parameters for the selected patient sample are identified in column 2260 ("Param") in data block 2210 of FIG. 3B.

Dropdown selector 2250 of the user interface allows a user to toggle among instruments and processing modes to select an optimal reference instrument and/or sample processing mode for the performance assessment. As shown in FIG. 3B, Bloodhound Instrument 1—Stat Mode is selected as the reference value; CBC parameters measured on Bloodhound Instrument 3—Stat Mode and Bloodhound Instrument 2—Open Port are compared against the selected reference value. The comparison data are reported as an absolute difference and percent difference in relation to the reference value. Referring to the mean cell volume (MCV) parameter 2260b, the reported MCV for the sample processed on Bloodhound Instrument 3—Stat Mode is 92.4 femtoliters. The absolute and percent difference between this measurement obtained on Bloodhound Instrument 3—Stat Mode and the reference value are 0.2 femtoliters and 0.3%, respectively, as reported in portion 2265 of data block 2210. Similarly, the absolute difference and percent difference for each of the CBC parameters measured on Bloodhound Instrument 3—Stat Mode and Bloodhound Instrument 2—Open Port with respect to the selected reference value are reported adjacent to each of the CBC parameter measurements identified in columns 2220 and 2230. Where comparison values exceed an acceptable tolerance range, the corresponding portion of data block can be highlighted to indicate the discrepancy. For example, the WBC parameter for Bloodhound Instrument 2—Open Port falls outside accepted values and is highlighted in column 2230 of data block 2210. As with the reference value selection, the user can configure the acceptable range for each CBC parameter absolute difference and percent difference value in relation to a selected reference value.

After a patient sample is processed on multiple instruments with multiple processing modes, reference value dropdown selector 2250 of the interface allows a user to toggle among instruments and processing modes to select an optimal reference value for the comparison data. Selecting a reference value on-the-fly through this feature enables the user to optimize the comparison data reporting format. Thus as the user selects different analyzers and processing modes corresponding to the data reported in data block 2210 for a new reference value, the absolute difference and percent difference values automatically update in the table of FIG. 3B. For example, if Bloodhound Instrument 2—Open Port is selected as the reference value, the absolute difference and percent difference values will automatically update for each of the CBC parameters measured on Bloodhound Instrument 1—Stat Mode and Bloodhound Instrument 3—Stat Mode in comparison to the new reference value. The reference value dropdown menu 2250 can also include a "Mean" setting to use as a reference value. If the mean is selected as the reference value for the CBC parameter data shown in FIG. 3B, then all three instruments and modes will have an absolute difference and percent difference reported against the mean for each CBC parameter value calculated from the three measured values of Bloodhound Instrument 1—Stat Mode, Bloodhound Instrument 2—Open Port, and Bloodhound Instrument 3—Stat Mode.

The systems and methods disclosed herein permit automated collection and reporting of measurement data across multiple instruments, as shown in FIG. 3B. The automatically collected data, in addition to spanning multiple instruments, can also correspond to multiple processing modes. In contrast, conventional blood analysis devices do not compare measured data among multiple instruments. As a result, the systems and methods disclosed herein permit a technician to rapidly and reliably detect instrument-related differences that arise from processing samples according to different modes, and also to assess the reliability of instruments compared to one another. To facilitate sharing of measurement data across multiple instruments, each of the instruments can include a communications interface connected to an electronic processor. Through the communications interface, each of the instruments can both transmit and receive information, including measurement data from processing patient and control samples. The systems disclosed herein can include a variety of different communications interfaces, including wireless interfaces (e.g., WiFi and/or cellular network communications interfaces) and wired interfaces (e.g., ethernet interfaces) for communicating across networks, including private networks, intranets, and the Internet.

In some embodiments, the data display interfaces disclosed herein can be configured to generate comparative plots showing measured data from multiple instruments over a period of time. As discussed above, such displays further enhance the ability of a technician to detect drift in an instrument or a specific processing mode over time by providing a readily-interpreted summary of a large number of measured data. In comparative plots, all of the data from a single instrument can be represented as a single line, or data measured using different processing modes on a single instrument can be represented as a series of lines corresponding to each of the modes. In some embodiments, the interfaces include a control selector that allows the technician to toggle the display of individual lines in a comparative plot on or off.

Figure 4:
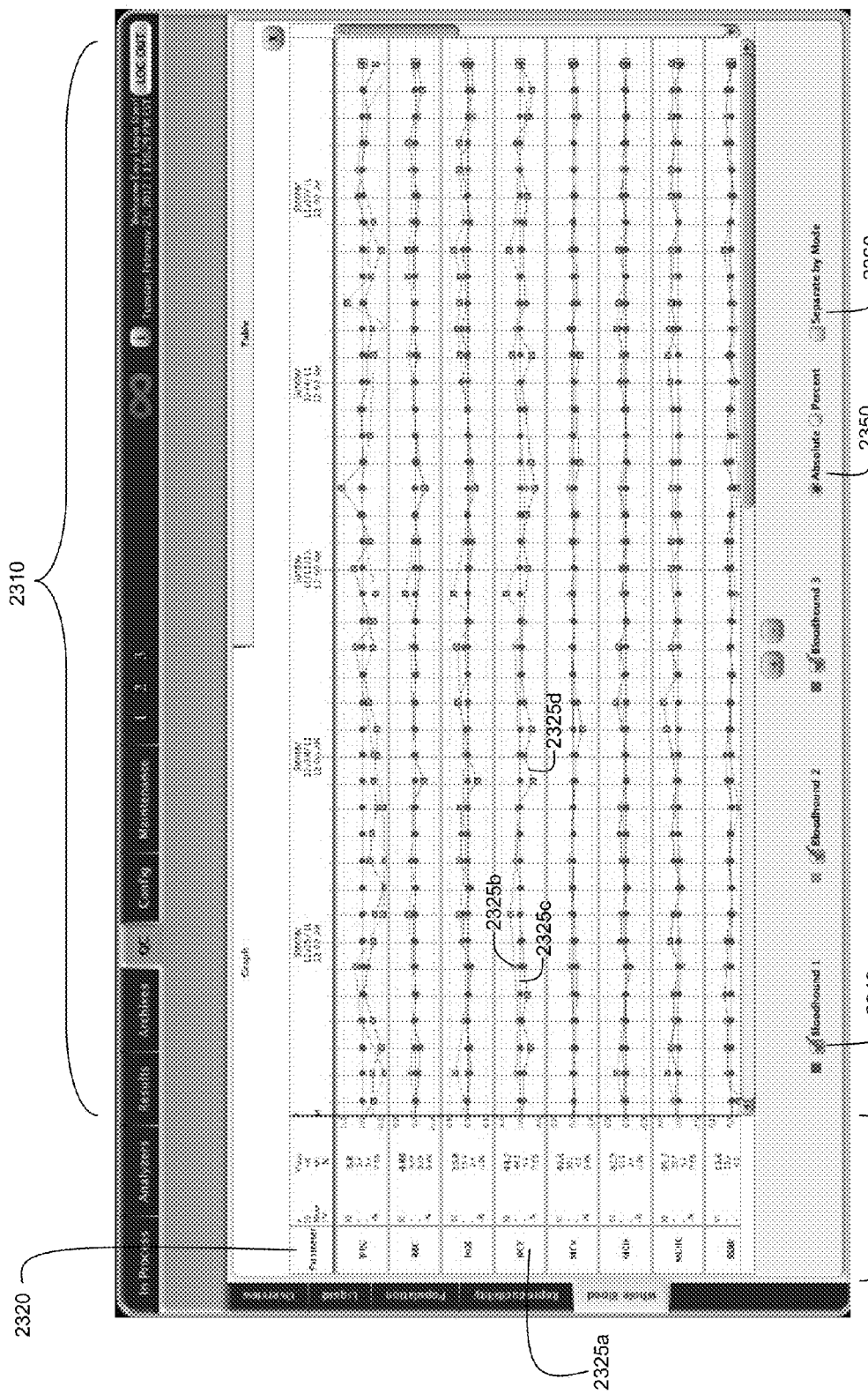
FIG. 4 is an image of a graphical user interface for reporting instrument-to-instrument comparison data.

With respect to the instrument-to-instrument comparison data reported in FIG. 3B, FIG. 4 shows an interface that reports such data in a format analogous to FIG. 1A. Each point within the plotted data shown in data block 2310 corresponds to a particular CBC parameter (listed in column 2320) measured on a patient sample (i.e., sample identifier No. 3250126 noted in FIG. 3B) at a given point in time. Double-clicking on (or otherwise selecting) any plotted point prompts the user with an option to exclude the particular test measurement from the report data set; once excluded, the point will not be included in the line plotted in FIG. 4 (and can, in some embodiments, be specially marked, for example by coloring the point differently). The point will also be excluded from the corresponding CBC parameter comparison calculations shown in FIG. 3B. For each CBC parameter shown in FIG. 4, the absolute difference between the measured value and the reference value is plotted as a function of time as indicated by the selected "Absolute" radio button in control 2350. Selecting the "Percent" radio button plots the data in a percentage difference format between the measured value and the reference value over time. Further, as discussed above in connection with FIGS. 3A-B, the interface shown in FIG. 4 can include user-selectable controls that scale (e.g., "zoom") the display of data in each plot or in all plots, and that control the location (e.g., left-hand or right-hand side) on each plot where new data points are plotted. The interface can also include a user control that, when activated, generates a scatter plot from the data shown in the interface, with each run color-coded to facilitate comparisons.

Comparison data for three instruments are shown in FIG. 4 as indicated by the selectors next to each of Bloodhound Instruments 1, 2, and 3 in portion 2340 of data block 2310. For each CBC parameter, comparison data for each instrument are plotted in an absolute difference format in comparison to reference values measured on Bloodhound Instrument 1. For example, comparison data for hematocrit values (HCT) measured on sample identifier No. 3250126 are reported for each of Instrument 1 (plot marked as 2325*c*), Instrument 2 (plot marked at 2325*b*), and Instrument 3 (plot marked as 2325*d*). In addition, the parameter plots for each instrument can be further sub-divided and displayed by processing mode. For example, assuming the instrument processed the patient sample in all three processing modes, each instrument-specific HCT plot 2325*b/c/d* can be expanded as three new plots, one for each HCT measurement obtained via normal, stat, and open port processing modes.

Figure 5A:
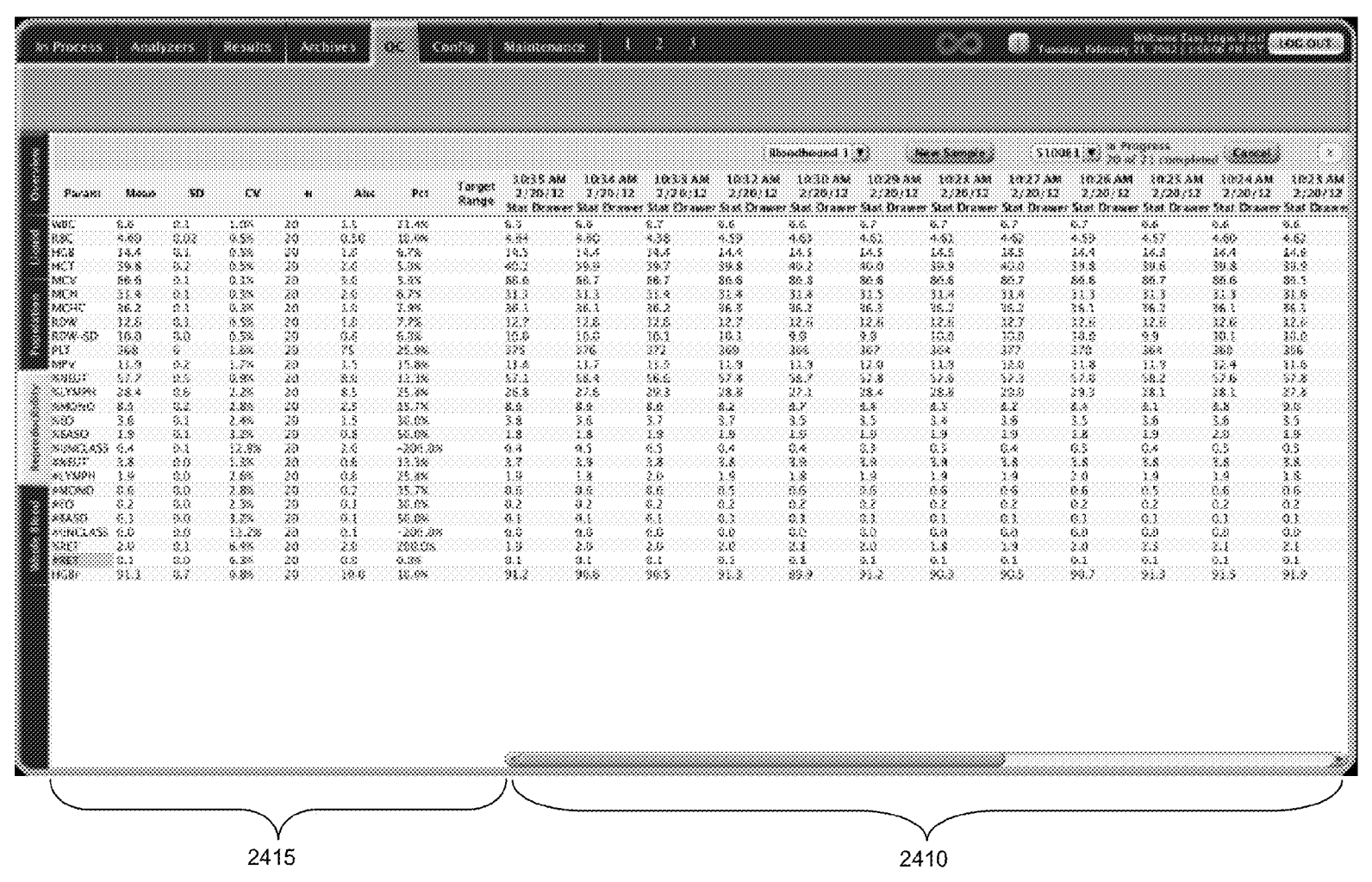

In some embodiments, the electronic processor of the blood analyzer can be configured to automatically calculate and report reproducibility data for the instrument using a patient sample. A single input command comprising sample identification information can be entered through the user interface to instruct the instrument to perform a reproducibility analysis on a given patient sample as shown in FIG. 5A. The configuration of the reproducibility analysis (e.g., number of times a sample is processed, CBC parameters reported, comparative measurements reported, etc.) to assess the instrument precision is user-defined. The single-input command initiating reproducibility testing and reporting on a particular patient sample eliminates the drawbacks associated with certain conventional reproducibility analysis tools such as the need for maintaining special bar codes, inputting additional instructions to define the reproducibility test requirements (e.g., sample processed twenty times), aggregating or manually manipulating multiple CBC data sets to generate a set of reproducibility data for all CBC data sets, or expensive middleware solutions required to process reproducibility data.

In addition to automatically performing the user-defined number of processing runs on a sample, the electronic processor is also configured to automatically re-perform any failed runs to ensure that the specified number of runs is completed for the analysis. Further, the electronic processor is configured to automatically tabulate data from each of the runs and compare the data to performance specifications for the instrument to determine whether a suitable level of reproducibility has been achieved. The electronic processor is also configured to re-perform failed runs only once to prevent the instrument from entering a non-terminating sampling cycle when the sample holder (e.g., a test tube) is empty.

Figure 5B:
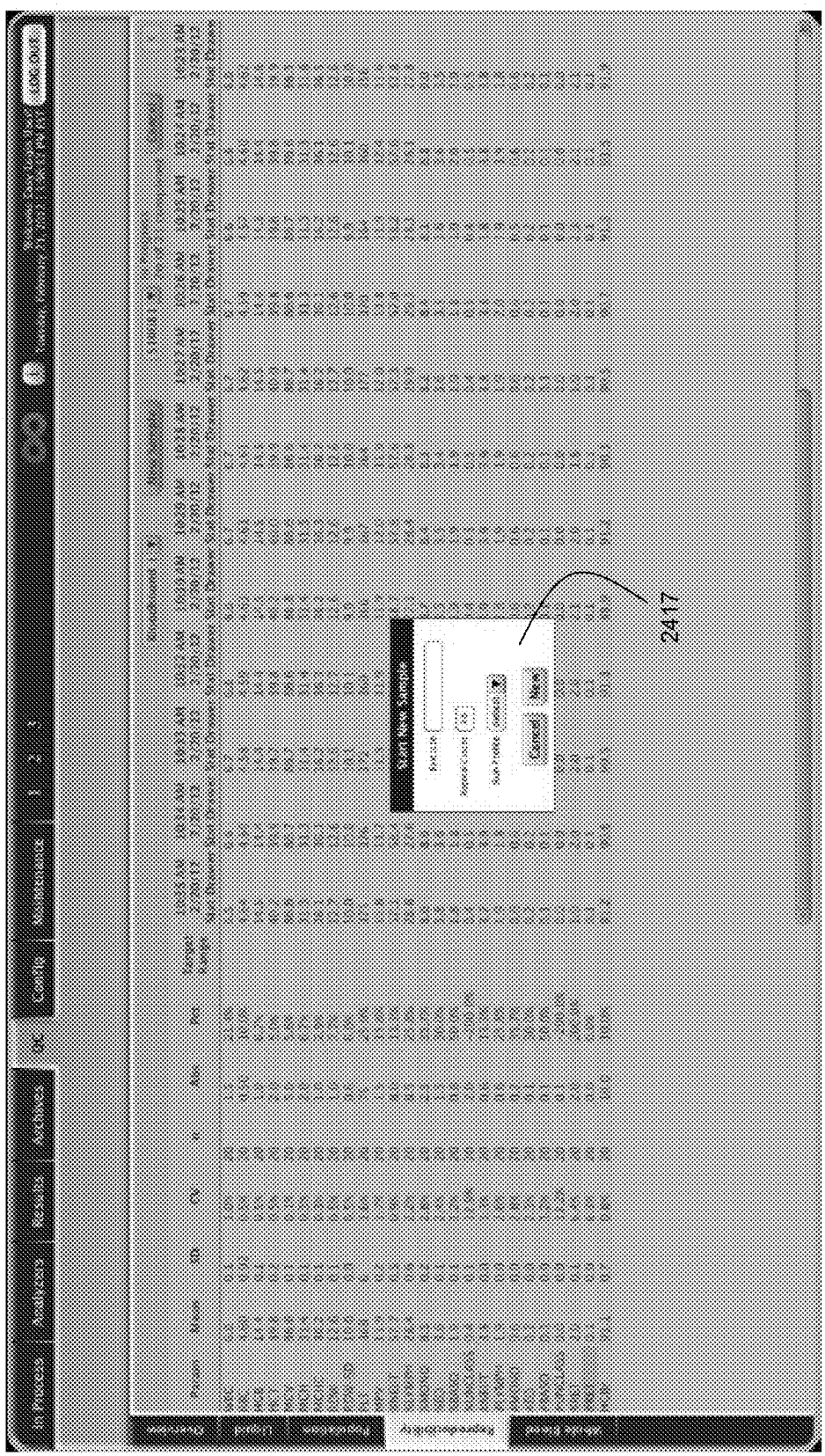

FIG. 5A shows reported CBC values and reproducibility data for a specific patient sample (No. 510081) processed on a particular instrument (e.g., Bloodhound Instrument 1 indicated in FIG. 5A) reported in data block 2410 and summary data block 2415, respectively. For each run, CBC parameters are measured for the sample, and the data are reported in distinct columns within data block 2410. The portion of data block 2410 shown in FIG. 5A includes twelve sets of CBC data for the sample, one set for each instance the instrument measured the CBC parameters for the sample. Summary data block 2415 includes reproducibility data corresponding to the measured CBC parameters. The reproducibility data includes a mean among all CBC parameters measured for the sample, standard deviation (SD) and coefficient of variation (CV) values, and number of times (n) the CBC parameters were measured for a given sample. A control box 2417 on the graphical user interface of display unit 110 (shown in FIG. 5B) prompts the user to identify a particular patient sample for mode-to-mode comparisons across multiple instruments. Control box 2417 functions in substantially the same manner as control box 2200 described previously.

Systems and Methods for Sample Imaging and Measurement

The display interfaces disclosed herein are designed to report a wide variety of information about samples processed using, e.g., automated blood analyzers. The electronic processor of such an analyzer is configured to perform any of the measurement, display, and/or reporting functions described herein. Before data from sample processing is displayed, however, the data is first obtained by processing the samples. The following systems and methods disclosed herein are configured to process samples in automated fashion to obtain numerical values of a wide variety of CBC parameters, including some or all of the parameters shown in Table 1.

Figure 6:
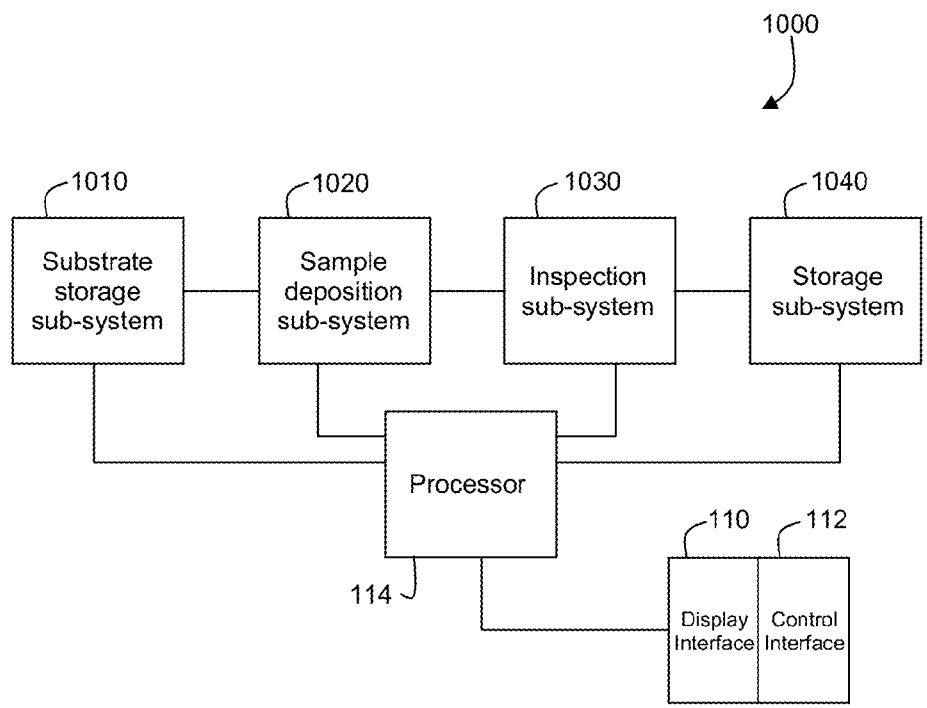
FIG. 6 is a schematic diagram of an automated system for sample analysis.

FIG. 6 shows a schematic diagram of an automated system 1000 for preparing and examining blood samples, including performing a CBC analysis. System 1000 includes multiple sub-systems for storing substrates, depositing samples on substrates, inspecting samples prepared on substrates, and storing prepared samples.

Substrate storage sub-system 1010 is configured to store substrates prior to the deposition of samples thereon. Substrates can include, for example, microscope slides, coverslips, and similar planar, optically transparent materials capable of supporting a sample such as, for example, cells from a sample of blood. The substrates can be formed from a variety of different amorphous or crystalline materials including various types of glasses. Sub-system 1010 can include a manipulator that selects individual substrates from a storage container and transfers the selected substrates to sample deposition sub-system 1020.

Sample deposition sub-system 1020 deposits a selected quantity of a sample of interest—such as a blood sample—onto a substrate. Sub-system 1020 includes, in general, a variety of fluid transfer components (e.g., pumps, fluid tubes, valves) configured to deposit the sample. Sub-system 1020 also includes fluid transfer components that expose the substrate to solutions of various types, including wash solutions, one or more stains that bind to the sample, fixing solutions, and buffer solutions. Sub-system 1020 can also feature fluid removal components (e.g., a vacuum sub-system) and a drying apparatus to ensure that the sample is fixed to the substrate. A substrate manipulator can transfer the substrate supporting the sample to inspection sub-system 1030.

Inspection sub-system 1030 includes various components for obtaining images of samples on substrates, and for analyzing the images to determine information about the samples. For example, inspection sub-system 1030 can include one or more light sources (e.g., lamps, arc lamps, light emitting diodes, laser diodes, and/or lasers) for directing incident light to a sample. Imaging sub-system 1030 can also include an optical apparatus (e.g., a microscope objective) for capturing transmitted and/or reflected light from a sample. A detector (e.g., a CCD detector) coupled to the optical apparatus can be configured to capture images of the sample. Information derived from analysis of the images of the sample can be stored on a variety of optical and/or electronic storage media for later retrieval and/or further analysis.

Following inspection, a substrate manipulator can transfer the substrate to storage sub-system 1040. Storage sub-system 1040 can label individual substrates, for example, with information relating to the source of the sample applied to the substrate, the time of analysis, and/or any irregularities identified during analysis. Storage sub-system can also store processed substrates in multi-substrate racks, which can be removed from system 1000 as they are filled with substrates.

As shown in FIG. 6, each of the various sub-systems of system 1000 can be linked to a common electronic processor 114. Processor 114 can be configured to control the operation of each of the sub-systems of system 1000 in automated fashion, with relatively little (or no) input from a system operator. Results from the analysis of samples can be displayed on system display interface 110 for a supervising technician. Control interface 112 (which in some embodiments can be integrated with display interface 110) permits the technician to issue commands to system 1000 and to manually review the automated analysis results.

Additional aspects and features of automated sample processing systems are disclosed, for example, in U.S. patent application Ser. No. 12/430,885, filed on Apr. 27, 2009, and U.S. patent application Ser. No. 13/293,050, filed on Nov. 9, 2011, the entire contents of each of which are incorporated herein by reference.

When multiple blood samples are analyzed automatically by system 1000, the system can generate a list of samples that merit further review by a technician. Samples can be flagged for further review based on a number of criteria. In some embodiments, system 1000 can be configured to identify various types of cells present in an individual blood sample, and the sample can be flagged for further analysis when the counted number of one or more of the various types of identified cells is either above or below a certain threshold number. For example, a sample can be flagged for further analysis if one or more of its lymphocyte count, monocyte count, neutrophil count, band neutrophil count, eosinophil count, basophil count, and/or red blood cell count exceeds or falls below a particular threshold value.

In certain embodiments, the sample can be flagged if one or more properties associated with the sample fall either above or below a certain threshold value. For example, system 1000 can be configured to measure various properties associated with the sample, including mean cell hemoglobin, mean cell volume, and hematocrit. If the values of any one or more of these measured sample properties exceeds or falls below a particular threshold value, the sample can be flagged. Methods and systems for measuring mean cell hemoglobin and mean cell volume are disclosed, for example, in the following applications, the entire contents of each of which are incorporated herein by reference: U.S. Provisional Patent Applications 61/476,179 and 61/476,170, both filed on Apr. 15, 2011; U.S. Provisional Patent Applications 61/510,710 and 65/510,614, both filed on Jul. 22, 2011; and U.S. patent application Ser. Nos. 13/446,967, 13/446,996, and 13/447,045, each filed on Apr. 13, 2012.

Once a sample has been flagged, system 1000 is configured to perform a series of automated steps to permit systematic visual inspection and assessment of the sample by a technician. The following exemplary description focuses on the review of red blood cells within a sample that has been flagged for further analysis. However, it should generally be understood that the systems and methods disclosed herein can be used for detailed inspection of a variety of different constituents within a blood sample, including white blood cells and/or platelets for example. Moreover, the systems and methods can be used for inspection of samples that have not been flagged (e.g., samples that have been determined to be "normal" according to various established criteria).

Figure 7:
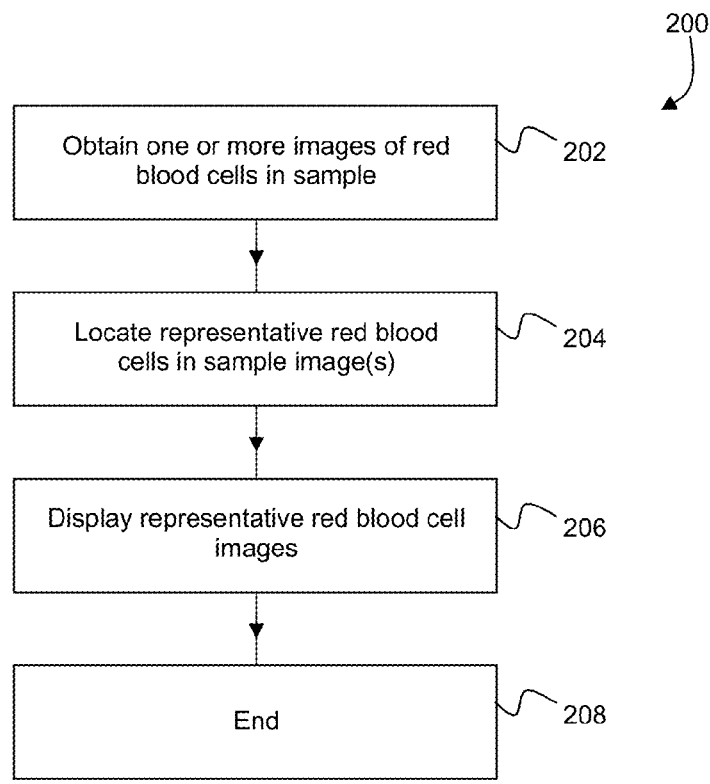
FIG. 7 is a flow chart showing a series of steps for obtaining and displaying images of red blood cells.

System 1000 is generally configured to perform a series of steps in order to obtain and organize images of red blood cells for review by a technician. FIG. 7 shows a flow chart 200 that includes a series of steps performed by system 1000 to obtain and display images of red blood cells. In a first step 202, system 1000 obtains one or more images of red blood cells in the sample. Red blood cells are typically prepared (as part of a sample) by applying a stain to the cells. The stain binds to the cell cytoplasm and serves as a marker for the cytoplasm in cell images. When a stained cell is illuminated with incident light, the stain absorbs a portion of the incident light. By detecting light transmitted through various regions of a sample (some of which correspond to stained red blood cells and some of which do not), the red blood cells can be readily identified.

Figure 8:
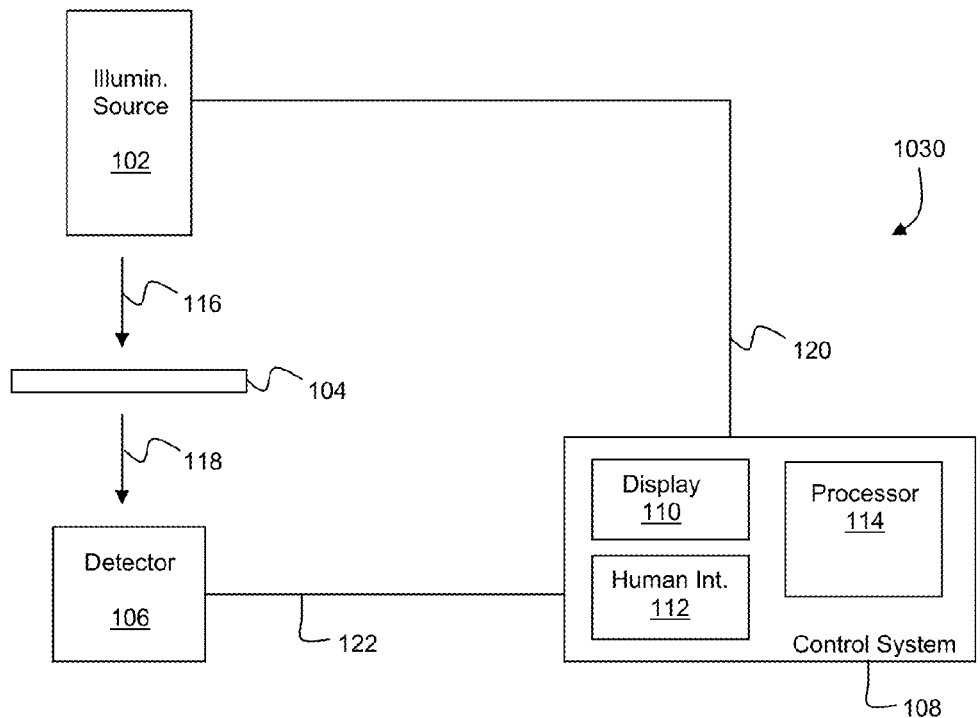
FIG. 8 is a schematic diagram of a system for obtaining sample images.

Inspection sub-system 1030 of system 1000 is configured to obtain the images of the red blood cells in the sample. FIG. 8 shows a schematic diagram of an embodiment of inspection sub-system 1030. Sub-system 1030 includes an illumination source 102, a detector 106, and an electronic control system 108. Electronic control system 108 typically includes electronic processor 114, display 110, and interface 112 (that is, the various components of sub-system 1030 are connected to electronic processor 114 of system 1000). Alternatively, in some embodiments, inspection sub-system 1030 can include one or more of a processor, a display, and an interface that is/are separate from the corresponding components of system 1000. Electronic control system 108 is connected to illumination source 102 and to detector 106 via control lines 120 and 122, respectively.

Assuming that a sample has been prepared by applying stain to the red blood cells therein, the prepared sample 104 (e.g., a stained blood sample on a microscope slide) is positioned automatically in proximity to source 102. Source 102 directs incident light 116 toward sample 104. A portion of the incident light passes through sample 104 as transmitted light 118 and is detected by detector 106. Transmitted light 118 forms an image of sample 104 on the active surface of detector 106; the detector captures the image, and then transmits the image information to electronic control system 108. In general, electronic control system 108 directs source 102 to produce incident light 116, and also directs detector 106 to detect the image of sample 104.

The process discussed above can be repeated to obtain multiple images of sample 104 (e.g., corresponding to multiple different regions of sample 104) if desired. However, the methods disclosed herein can operate using information derived from only a single sample image. Electronic control system 108 can adjust the wavelength of incident light 116 produced by source 102 prior to acquiring a new image. As such, the multiple images of sample 104 can correspond to different wavelengths of incident light 116 and therefore, different wavelengths of transmitted light 118.

Illumination source 102 can include one source or a plurality of the same or different sources. In some embodiments, source 102 can include multiple light emitting elements such as diodes (LEDs), laser diodes, fluorescent lamps, incandescent lamps, and/or flashlamps. For example, source 102 can include four LEDs having output wavelengths in the red, yellow, green, and blue regions of the electromagnetic spectrum, respectively (e.g., 635, 598, 525, and 415 nm). In certain embodiments, source 102 can include one or more laser sources. Instead of having multiple light emitters, in other embodiments, source 102 can include a single broadband emitter than can be configured to alter its output wavelength (e.g., under the control of electronic control system 108). For example, source 102 can include a broadband source (e.g., a laser source, or a white-light-emitting LED source) coupled to a configurable filter system (e.g., a plurality of mechanically adjustable filters, and/or a liquid-crystal-based electronically-adjustable filter) that produces a variable output spectrum under the control of system 108. In general, source 102 does not output illumination light 116 at a single wavelength, but in a band of wavelengths centered around a central wavelength (e.g., the wavelength of maximum intensity in the band). When the discussion herein refers to the wavelength of illumination light 116, this reference is to the central wavelength of the illumination band.

Detector 106 can include a variety of different types of detectors. In some embodiments, detector 106 includes a charge-coupled device (CCD). In certain embodiments, detector 106 can include photodiodes (e.g., a two-dimensional photodiode array). In some embodiments, detector 106 can include other light-sensitive elements such as CMOS-based sensors and/or photomultipliers. Detector 106 can also include one or more filtering elements, as described above in connection with source 102. In some embodiments, sample images corresponding to different wavelengths are obtained by illuminating sample 104 with illumination light 116 having a relatively broad distribution of wavelengths, and then filtering transmitted light 118 to select only a portion of the transmitted light corresponding to a small band of the wavelengths. Filtering can be performed on either or both the illumination side (e.g., in source 102) and the detection side (e.g., in detector 106) to ensure that images obtained using detector 106 each correspond to a specific distribution of light wavelengths with a particular central wavelength.

In certain embodiments, a broadband illumination source can be used together with a color camera (e.g., a camera configured to measure light in three different wavelength bands, such as red, green, and blue bands) to obtain sample images at multiple different wavelengths. The images corresponding to the different wavelength bands can be used separately or in combination in the methods disclosed herein.

Sub-system 1030 and/or system 1000 can also include a communications interface (not shown). The communications interface can be a wireless and/or wired interface connected to processor 114, and configured to transmit and receive instructions. In particular, the interface can enable system 1000 to communicate over a variety of networks, including private networks, intranets, and the Internet. Multiple blood analyzers can communicate with one another over such networks, and can transfer data including measurement results to one another. In this manner, a single blood analyzer can display results from multiple instruments, as described above. The blood analyzers can also transfer data to a centralized storage facility or medium such as a database, and can retrieve data from the storage facility medium. In this way, a single analyzer can retrieve measurement results from multiple instruments from the database, and display the results on a single display for assessment by a technician.

In some embodiments, electronic processor 114 can be configured to convert pixel intensity values in the measured sample image(s) to optical density values. In the sample image(s), the transmitted light intensity T(x,y) at a given image pixel (x,y) is related to the absorption coefficient α and the path length $\epsilon(x,y)$ of the incident light through the portion of the sample corresponding to that pixel:

$$T(x,y)=10^{\mu \cdot \epsilon(x,y)}$$

For each pixel in an image, the ratio of the pixel intensity to the maximum possible pixel intensity (e.g., pixel intensity/ 255 at 8-bit resolution) represents the fraction of light transmitted at the spatial location of the pixel. The fraction of transmitted light can be expressed in optical density (OD) units by taking the logarithm of the above equation:

$$OD(x,y)=-\log(T)=a \cdot s(x,y)$$

This process can be repeated for each pixel in the sample image. In this way, the optical density at each pixel in each image corresponds to the total amount (e.g., the product of the absorption coefficient and the thickness) of absorbing material in the sample at the location corresponding to the pixel.

Figure 9:
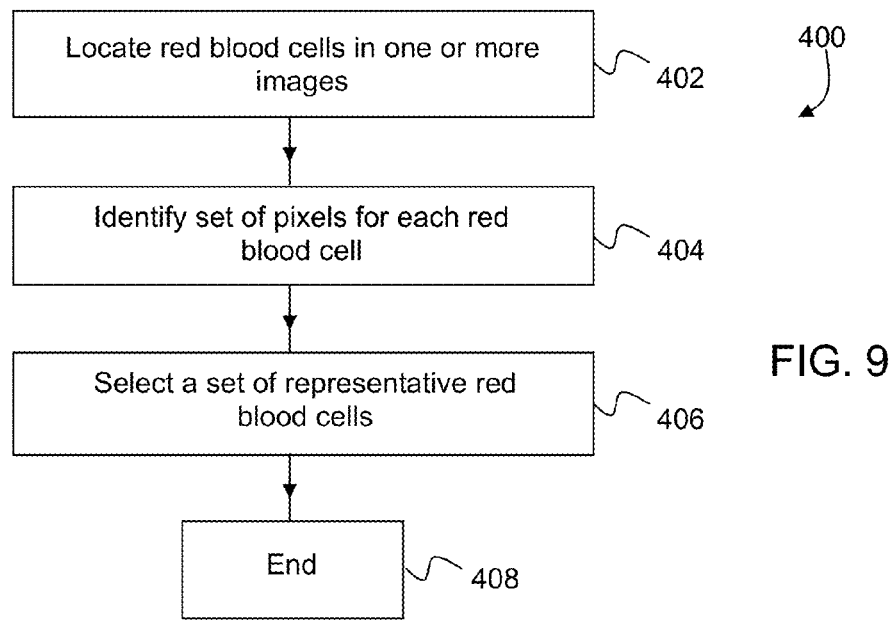
FIG. 9 is a flow chart showing a series of steps for locating red blood cells in a sample image.

Returning to FIG. 7, the next step 204 in flow chart 200 includes locating representative red blood cells in the sample image(s) obtained in step 202. The process of locating representative red blood cells typically proceeds according to a series of steps. FIG. 9 shows a flow chart 400 that includes multiple steps for locating red blood cells in a sample image. First, in step 402 of FIG. 9, system 1000 locates red blood cells in one or more sample images for further processing. Red blood cells typically absorb blue light (e.g., 415 nm) due to the presence of hemoglobin in the cells. White blood cells, however, do not contain hemoglobin and therefore do not absorb blue light in the same manner as red blood cells. An image of the sample acquired under blue light can be used to identify red blood cells; in such an image, red blood cells appear as dark objects, whereas white blood cells appear as significantly fainter objects, and can be excluded from further consideration.

In some embodiments, a thresholding step can be used to ensure that system 1000 identifies only red blood cells for further analysis. For example, system 1000 can utilize only image pixels below an intensity (or gray) value of 160 (for images captured at 8-bit resolution). Other intensity value thresholds ranging from 100 to 180 can be used to identify red blood cells from the image, while excluding white blood cells from further analysis.

Next, in step 404, system 1000 identifies a set of pixels for each red blood cell in the sample image. A variety of different methods can be used to identify sets of pixels associated with the cells. For example, in some embodiments, system 1000 performs the identification step using a connected components labeling process. This process correlates individual pixels from the sample image to an object in the image. For example, any two pixels in the image not separated by a pixel assigned to the background are assigned to the same cell.

In addition, in some embodiments, system 1000 can exclude pixels positioned within a border region of a cell. Typically, such exclusions are used when calculating quantitative metrics relating to the cell, but the excluded pixels are otherwise retained within the set of pixels corresponding to the cell for purposes of image display. In some embodiments, however, the excluded pixels are purged from the set of pixels corresponding to the cell.

Red blood cells often have thick, dark borders due to the manner in which these cells refract illumination light. Optical densities for these pixels are typically unreliable due to this refraction. After completing the connected components labeling process, system 1000 can apply a pixel erosion mask to the identified cells to remove the outermost n layers of pixels (e.g., the pixel(s) that correspond to the boundary region where refraction is greatest). In general, the pixel erosion mask can be selected to remove any number n of pixel layers (e.g., one pixel layer or more, two pixel layers or more, three pixel layers or more, four pixel layers or more, five pixel layers or more, six pixel layers or more, eight pixel layers or more, ten pixel layers or more) depending on the magnification of the image. It has been determined experimentally that a pixel erosion mask comprising the outermost 0.5 μm for the red cell perimeter is generally suitable for significantly reducing erroneous contributions to the measurement of cell volume and hemoglobin content for red blood cells where each pixel corresponds to a portion of the cell that is 0.148 μm×0.148 μm. Utilizing the sets of pixels corrected by erosion masks, various cell features can be measured.

In step 406, system 1000 continues the process of identifying a set of representative red blood cells from the sample image(s) by assessing the size and shape of red blood cells. In general, step 406 functions to discard partial cells, overlapping cells, cell clusters, platelets, and non-cellular artifacts from inclusion in the set of representative red blood cells. For example, cells that are either cut off by, or touching, the edge of the image frame can be excluded from further analysis, thereby preventing inaccurate measurements. In addition, misshapen cells—which can exhibit variations in the determined cell volume that are related to their non-standard shapes—can be excluded from the analysis. Further, measurement results obtained from overlapping cells, which can be unreliable when used for calculating metrics such as cell volumes or constituent content, can be precluded from the set of representative cells. For these reasons, the shapes of each of the identified cells are checked in step 406, and misshapen and/or overlapping cells are excluded from further analysis.

Figure 10:
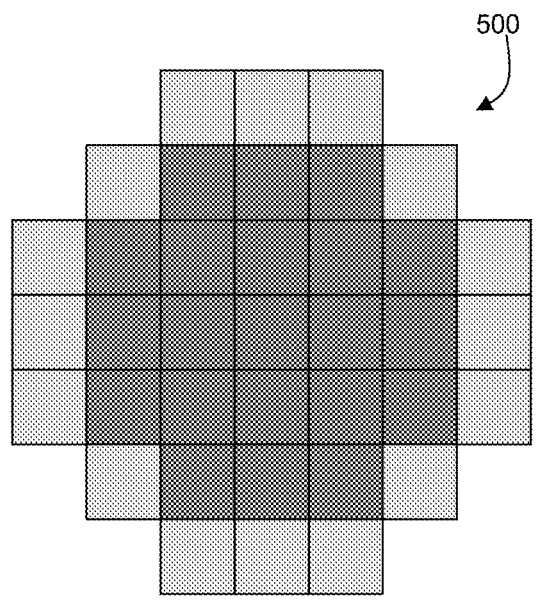
FIG. 10 is a schematic image of a cell.

A variety of different methods can be used to check the shape of the identified cells. For example, in some embodiments, the shape of each cell can be checked by comparing the perimeter and the area of the cell. FIG. 10 shows a schematic diagram of such a comparison. In FIG. 10, a cell 500 has been identified as a set of pixels in a sample image. The pixels corresponding to the boundary of cell 500 are shaded lighter in FIG. 10 than the interior pixels for purposes of demonstration—they do not necessarily appear this way in the actual image. The area of cell 500 can be determined by counting the number of pixels in the set.

The cell perimeter is determined from the boundary pixels using the set of pixels corresponding to cell 500. This can be accomplished by connecting a line through the center of each perimeter pixel to create a polygon in the image and measuring the perimeter of the polygon. The ratio of this cell perimeter value squared to the cell area value (i.e., the area of the polygon) is determined to check the shape of the cell. The value of this ratio is $4\pi$ for an ideal, perfectly circular cell. The value of the ratio increases as the cell shape departs from a circular outline. Using this criterion, cells with a ratio of the perimeter squared to the area, which exceeds the minimum value of $4\pi$ by a threshold amount or more, are excluded from further analysis. Typically, the threshold amount is a percentage of the minimum value of $4\pi$ (e.g., 5% or more, 10% or more, 15% or more, 20% or more, 25% or more).

In addition to excluding misshapen individual cells from further analysis, the procedure discussed above can also exclude overlapping cells. In sample images, overlapping cells typically appear as large, misshapen individual cells (with variations in transmitted light intensity due to the increased thickness of material through which the incident light propagates). Overlapping cells are generally identified as large single cells with irregular boundaries when analysis algorithms are applied to such images. As such, when the comparison of the cell perimeter and area is performed, the ratio falls well beyond the threshold for allowable variance from the ideal value, and the overlapping cells are excluded.

Figure 11:
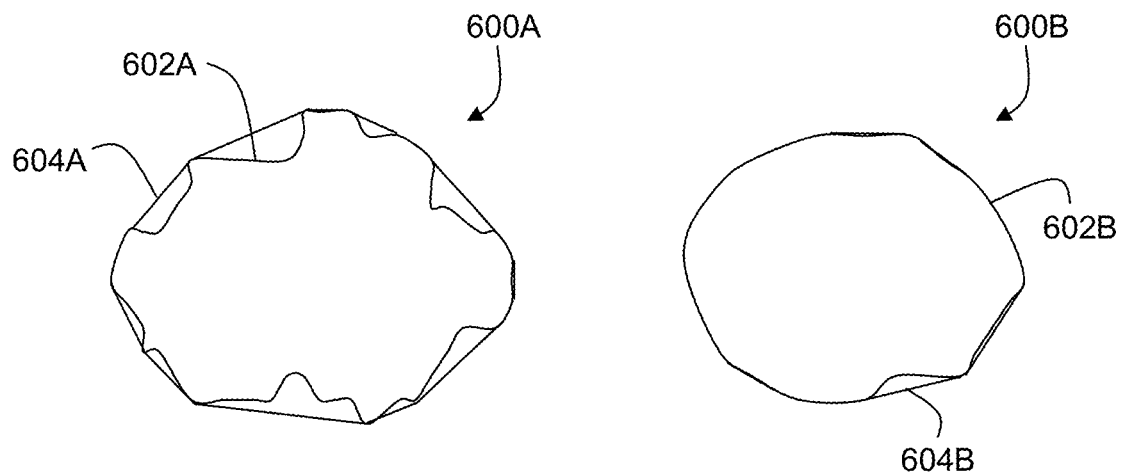
FIG. 11 is a schematic diagram showing two cells and convex hulls determined for each of the cells.

Another method for checking the shape of identified cells utilizes the convex hull of the polygonal representation of the cell outline described above and compares the area enclosed by the convex hull to the cell area determined from the image pixels. A high ratio of convex hull area to cell area can be used to identify irregularly shaped cells and exclude such cells from further analysis. FIG. 11 is a schematic diagram that includes two cells 600A and 600B. The perimeters of cells 600A and 600B are marked as 602A and 602B, respectively, in FIG. 11. A convex hull 604A is drawn around cell 600A, and a convex hull 604B is drawn around cell 600B. As shown in FIG. 11, the discrepancy between the convex hull area and the cell area is greater for cell 600A than for cell 600B. Given the high degree of irregularity for cell 600A, cell 600A can be excluded from the set of representative red blood cells.

In some embodiments, cell area measurements can be used in step 406 to exclude artifacts and overlapping cells from the set of representative blood cells. For example, only cells with an area ranging from 35 square microns to 65 square microns can be considered for red blood cell volume measurements. Imaged objects with an area less than 35 square microns are typically not red blood cells, but artifacts, such as a speck of dust in the sample. Similarly, imaged objects with an area greater than 65 square microns are typically not red blood cells; such object might correspond to a blob of stain or to several overlapping cells. While the foregoing example describes a 35 to 65 square micron area range, other ranges can be used to select red blood cells for measurement (e.g., 20 square microns to 80 square microns), and the range can be scaled based on the average cell size in the sample, thereby accounting for patient-to-patient variability. It has been determined experimentally that while the 35-to-65 square micron range can exclude some red blood cells, such range is more effective at removing artifacts from the sample image as compared to the 20-to-80 square micron range.

Optical density values can be used to select the set of representative red blood cells in the sample. For example, if the mean optical density value of an object imaged under blue light is too low, the object may be a white blood cell nucleus instead of a red blood cell. A mean optical density threshold can be used (e.g., mean optical density less than or equal to 0.33) for images acquired using blue light to exclude white blood cells from the set of representative red blood cells for the sample (e.g., a cell with a mean optical density less than or equal to 0.33 is likely to be a white blood cell). For images acquired under blue or yellow illumination, a mean optical density value for an object exceeding a certain threshold (e.g., mean optical density greater than or equal to 0.66) can be used to identify stacked, overlapping, and/or clustered red blood cells, which can be excluded from further analysis (e.g., a red blood cell with a mean optical density greater than or equal to 0.66 is likely to be overlapping another red blood cell). The process shown in FIG. 4 terminates at step 408 with the final determination of a set of representative cells for further analysis.

Returning to FIG. 7, after the representative red blood cells are located in step 204, the representative cells are displayed to a technician on display 110 in step 206. In some embodiments, all such cells are displayed. In certain embodiments, only a subset of the cells located in step 204 are displayed. The subset of cells that are displayed can be selected at random, and the number of cells in the subset is user-selectable. For example, the subset of representative cells displayed can include 100 cells or more (e.g., 250 cells or more, 500 cells or more, 750 cells or more, 1000 cells or more, 2000 cells or more, 5000 cells or more, 10,000 cells or more). Following display of the representative red blood cell images in step 206, the procedure shown in flow chart 200 terminates at step 208.

As discussed above, in some embodiments, the subset of representative cells that are displayed in step 206 does not necessarily correspond to the set of representative cells that are used to determine quantitative metrics for the blood sample. In particular, it can be important to display for the technician cells that have abnormal shapes, optical densities, inclusions, and other irregular attributes. Although such cells are typically not used in quantitative determinations such as the calculation of mean cell hemoglobin and mean cell volume, a technician viewing images of such irregular cells can infer the presence of certain conditions in a blood sample from irregular cells. As such, while cells that are unsuitable for use in quantitative calculations can be determined using the methods disclosed above, in certain embodiments the subset of cells that are displayed in step 206 includes some or all of these "unsuitable" cells.

A variety of different methods can be used to display cell images to technician for review. Methods and systems for the display of images are disclosed, for example, in U.S. Provisional Patent Application No. 61/498,456, filed on Jun. 17, 2011, in U.S. Provisional Patent Application No. 61/510, 696, filed on Jul. 22, 2011, and in U.S. patent application Ser. No. 13/526,223, filed on Jun. 18, 2012. The entire contents of each of the foregoing applications are incorporated herein by reference.

In some embodiments, cell images can be displayed in an image block and sorted according to a variety of criteria, including the presence or absence of inclusions in the cells and properties of the inclusions such as size. Inclusion detection can be performed at the same time that the cell images are analyzed to determine size, optical density, and other properties of the cells (e.g., in step 406 of FIG. 9).

Various methods can be used to detect the presence of inclusions in a cell once a set of pixels corresponding to the cell has been identified. For example, a first method identifies possible inclusions based on the optical density of pixels in the cell image. In particular, each pixel in a red blood cell image is segmented into one of three classes: normal red blood cell, central pallor, and possible inclusion. Pixels corresponding to the normal portion of the red blood cell can be identified in relatively straightforward fashion because these pixels have been observed experimentally to have a narrow range of optical densities. Accordingly, by establishing upper and lower thresholds for normal red blood cell pixels, these pixels can be identified in the cell image.

The remaining pixels in the image correspond to either the central pallor or to possible inclusions. In general, pixels with low optical densities correspond to the central pallor, while pixels with large optical densities correspond to possible inclusions. Thus, individual pixels can readily be identified as corresponding to possible inclusions based on their optical density.

A second method for identifying possible inclusions involves two separate steps. In a first step, pixels that correspond to the central pallor are identified by examining an image of the cell corresponding to illumination with blue light (e.g., 415 nm). Pixels in the blue image are examined individually, and pixels for which the optical density both: (a) exceeds a threshold value based on the average optical density in the blue image; and (b) is either closer to the largest optical density in the blue image than to the average optical density in the blue image, or that differs from the maximum optical density in the blue image by less than two standard deviations, are assigned to the central pallor.

Pixels corresponding to possible inclusions are determined in a second step. First, pixels that correspond to areas of large optical density (according to a user-selectable threshold value) in the blue image are removed from further consideration, because while refraction-related artifacts appear dark in blue images, genuine inclusions in general do not appear as dark in blue images. Then, for each remaining pixels, the optical densities in the yellow (Y, e.g., 598 nm), green (G, e.g., 525 nm), and blue (B) images are used to calculate a value of the quantity P:

$$P = |Y - |G - B||$$

A large value of the quantity P for a pixel effectively identifies a pixel that is dark in the yellow and green images, but light in the blue image. An image of the cell based on the values of the quantity P is constructed, and an edge detection algorithm is run on the image. For each pixel in the image, if the pixel: (a) has a large optical density value in the yellow image, Y; (b) has a large value of P; and (c) was identified as corresponding to an edge by the edge detection algorithm, then the pixel is identified as belonging to a possible inclusion.

Pixels corresponding to possible inclusions can then be grouped into inclusion fragments based on the presence or absence of pixels of other types between them. The number of inclusion fragments can be determined and used to further refine the identification of possible inclusions. For example, where a cell contains a large number of inclusion fragments (e.g., larger than a user-selectable threshold number), the possible inclusions can be identified as being due to imaging aberrations or other phenomena such as basophilic stippling, and further analysis of possible inclusions in the cell can be discontinued.

For cells in which possible inclusions remain likely, features of the inclusions such as perimeter, area, and shape can be determined using the pixel-based methods disclosed above. Cells featuring inclusions can then be sorted in the image block according to any of the various features determined for the inclusions.

Hardware and Software Implementation

The method steps and procedures described herein can be implemented in hardware or in software, or in a combination of both. In particular, electronic processor 114 can include software and/or hardware instructions to perform any of the method steps disclosed above. The methods can be implemented in computer programs using standard programming techniques following the method steps and figures disclosed herein. Program code is applied to input data to perform the functions described herein. The output information is applied to one or more output devices such as a printer, or a display device, or a web page on a computer monitor with access to a website, e.g., for remote monitoring.

Each program is preferably implemented in a high level procedural or object oriented programming language to communicate with a processor. However, the programs can be implemented in assembly or machine language, if desired. In any case, the language can be a compiled or interpreted language. Each computer program can be stored on a storage medium or device (e.g., an electronic memory) readable by the processor, for configuring and operating the processor to perform the procedures described herein.

For purposes of this disclosure, "activating" a user-selectable control displayed on an interface can include (but is not limited to) "clicking" on the control using a pointer or other indicator (e.g., a mouse pointer), positioning a pointer so that it overlays the control, highlighting the control by using a pointer or an encircling indicator, and/or positioning an indicator on the interface so that the control is selected.

Interfaces that can be used to display cell images (e.g., as user-selectable controls) include a wide variety of displays (e.g., CRTs, LED-based displays, liquid crystal-based displays, projection displays). Interfaces can be touch-sensitive, allowing a user to interact directly with the displayed elements. Alternatively, or in addition, additional system components (e.g., keyboards, pointing devices) can permit a user to manipulate elements displayed on the interface.

Figure 12:
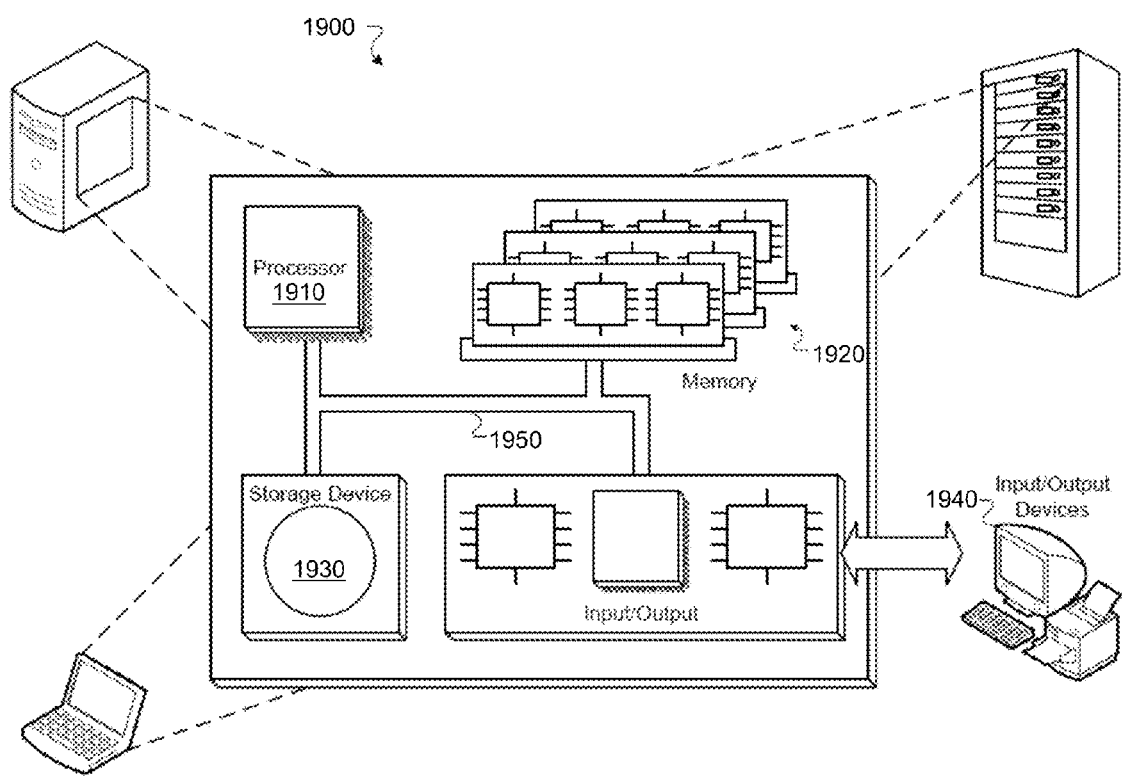
FIG. 12 is a schematic diagram of a computing system for displaying measurement results for assessing blood analyzer performance.

FIG. 12 is a schematic diagram of a computer system 1900 that can be used to control the operations described in association with any of the computer-implemented methods described herein, according to certain embodiments. The system 1900 includes a processor 1910, a memory 1920, a storage device 1930, and an input/output device 1940. Each of the components 1910, 1920, 1930, and 1940 are interconnected using a system bus 1950. The processor 1910 is capable of processing instructions for execution within the system 1900. In some embodiments, the processor 1910 is a single-threaded processor. In other embodiments, the processor 1910 is a multi-threaded processor. The processor 1910 is capable of processing instructions stored in the memory 1920 or on the storage device 1930 to display graphical information for a user interface on the input/output device 1940. The processor 1910 can be substantially similar to the processor 114 described above with reference to FIGS. 6 and 8. Moreover, the processor can be a part of a blood analyzer, part of a viewing station connected to or associated with a blood analyzer, or common to both a blood analyzer and a viewing station.

The memory 1920 stores information within the system 1900. In some embodiments, the memory 1920 is a computer-readable medium. The memory 1920 can include volatile memory and/or non-volatile memory.

The storage device 1930 is capable of providing mass storage for the system 1900. In general, the storage device 1930 can include any non-transitory tangible media configured to store computer readable instructions. In one embodiment, the storage device 1930 is a computer-readable medium. In various different embodiments, the storage device 1930 may be a floppy disk device, a hard disk device, an optical disk device, or a tape device.

The input/output device 1940 provides input/output operations for the system 1900. In some embodiments, the input/output device 1940 includes a keyboard and/or pointing device. In some embodiments, the input/output device 1940 includes a display unit for displaying graphical user interfaces. In some embodiments, the input/output device 1940 includes one or more of the display 110 and interface 112 described above with reference to FIGS. 6 and 8.

The features described can be implemented in digital electronic circuitry, or in computer hardware, firmware, or in combinations of them. The features can be implemented in a computer program product tangibly embodied in an information carrier, e.g., in a machine-readable storage device, for execution by a programmable processor; and features can be performed by a programmable processor executing a program of instructions to perform functions of the described embodiments by operating on input data and generating output. The described features can be implemented in one or more computer programs that are executable on a programmable system including at least one programmable processor coupled to receive data and instructions from, and to transmit data and instructions to, a data storage system, at least one input device, and at least one output device. A computer program includes a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Various software architectures can be used for implementing the methods and systems described in this application. For example, a publish/subscribe messaging pattern can be used in implementing the methods and systems described herein. In the case of publish/subscribe messaging, the system includes several hardware and software modules that communicate only via a messaging module. Each module can be configured to perform a specific function. For example, the system can include one or more of a hardware module, a camera module, and a focus module. The hardware module can send commands to the imaging hardware implementing the fast auto-focus, which in turn triggers a camera to acquire images. In some embodiments, the hardware module can include the control system 108 described above with reference to FIG. 8.

A camera module can receive images from the camera and determine camera parameters such as shutter time or focus. Images can also be buffered in the computer's memory before being processed by the camera module. When performing the initial search for the tilt of the slide, the camera module can also send a message interrupting the hardware module when it has seen enough images to determine the proper shutter time or focus. In some embodiments, the camera module includes the detector 106 described above with reference to FIG. 8.

The system can also include a focus module that can be implemented as software, hardware or a combination of software and hardware. In some embodiments, the focus module examines all the frames in a stack and estimates how far the stack is from the ideal or ideal focal distance. The focus module can also be responsible for assigning a focus score to each frame in a stack of images.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. Computers include a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Alternatively, the computer can have no keyboard, mouse, or monitor attached and can be controlled remotely by another computer The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

The processor 1910 carries out instructions related to a computer program. The processor 1910 can include hardware such as logic gates, adders, multipliers and counters.

The processor 1910 can further include a separate arithmetic logic unit (ALU) that performs arithmetic and logical operations.

OTHER EMBODIMENTS

A number of embodiments have been described. Nevertheless, it will be understood that various modifications may be made without departing from the spirit and scope of the disclosure. In particular, features disclosed herein in connection with specific embodiments can generally be included in other embodiments, and particular features disclosed herein can generally be used in combination with any of the other features of any of the embodiments disclosed herein. Accordingly, other embodiments are within the scope of the following claims.

What is claimed is:

1. A method for displaying measured values of a complete blood count ("CBC") parameter, the method comprising:
displaying the measured values of the CBC parameter obtained from a plurality of samples from a first lot of a quality control composition on a display device, wherein the displaying comprises displaying a plurality of markers as user-selectable controls corresponding to the measured values from the first lot on a plot comprising a two dimensional coordinate system on the display device, wherein each marker represents a mean value of corresponding measured values of the CBC parameter for more than one of the samples, and wherein the two dimensional coordinate system comprises a first dimension corresponding to a time at which measured values of the CBC parameter were obtained, and a second dimension corresponding to a numerical value of the CBC parameter;
monitoring the display device to determine when a user activates a member of the plurality of markers; and
when activation of a member of the plurality of markers is detected, displaying the measured values of the CBC parameter for the more than one of the samples corresponding to the activated marker.

2. The method of claim 1, wherein the markers each have an associated coordinate value along the second dimension, the method further comprising determining the associated coordinate value along the second dimension for each marker based on a difference between the mean value represented by the marker and a reference value of the CBC parameter for the first lot.

3. The method of claim 2, wherein the reference value of the CBC parameter corresponds to an average of the measured values of the CBC parameter for the first lot.

4. The method of claim 1, further comprising:
displaying measured values of the CBC parameter obtained from a plurality of samples from a second lot of a quality control composition, wherein the displaying comprises displaying a second plurality of markers as user-selectable controls corresponding to the measured values from the second lot on the plot,
wherein each marker of the second plurality of markers represents a mean value of corresponding measured values of the CBC parameter for more than one of the samples from the second lot; and
wherein when a member of the second plurality of markers is activated, the measured values of the CBC parameter for the more than one of the samples of the second lot corresponding to the activated marker are displayed.

5. The method of claim 4, wherein the markers corresponding to the samples of the second lot each have an associated coordinate value along the second dimension, the method further comprising determining the associated coordinate value along the second dimension for each marker corresponding to the samples of the second lot based on a difference between the mean value represented by the marker and a reference value of the CBC parameter for the second lot.

6. The method of claim 5, wherein the reference value of the CBC parameter for the second lot corresponds to an average of the measured values of the CBC parameter for the second lot.

7. The method of claim 1, further comprising displaying successive markers in a temporal sequence extending parallel to the first dimension and in a direction toward the second dimension.

8. The method of claim 7, further comprising displaying a user-selectable control associated with the first dimension, wherein when activated, the user-selectable control allows the user to adjust the direction toward which the temporal sequence of successive markers extends.

9. The method of claim 1, further comprising displaying on the plot one or more indicators defining a standard range of values for the CBC parameter.

10. The method of claim 9, further comprising:
displaying members of the plurality of markers that correspond to mean values within the standard range in a first color on the plot; and
displaying members of the plurality of markers that correspond to mean values outside the standard range in a second color different from the first color on the plot.

11. The method of claim 1, wherein the user interface comprises a user-selectable control for selecting multiple markers, the method further comprising, when multiple markers are selected by activating the user-selectable control for selecting multiple markers, displaying statistical information about a distribution of values of the CBC parameter associated with the selected markers.

12. The method of claim 1, further comprising, at each of a plurality of different measurement times, determining a mean value of the measured values of the CBC parameter corresponding to the first lot, and displaying a marker on the plot that corresponds to the mean value.

13. A system for displaying measured values of a complete blood count ("CBC") parameter, the system comprising:
a user interface; and
an electronic processor configured to
display measured values of the CBC parameter obtained from a plurality of samples from a first lot of a quality control composition, wherein the displaying comprises displaying a plurality of markers as user-selectable controls corresponding to the measured values from the first lot on a plot comprising a two dimensional coordinate system on the user interface, wherein each marker represents a mean value of corresponding measured values of the CBC parameter for more than one of the samples, and wherein the two dimensional coordinate system comprises a first dimension corresponding to a time at which values of the CBC parameter were obtained, and a second dimension corresponding to a numerical value of the CBC parameter;
monitor the user interface to determine when a user activates a member of the plurality of markers; and when activation of a member of the plurality of markers is detected, display the measured values of the CBC parameter for the more than one of the samples corresponding to the activated marker.

14. The system of claim 13, wherein the markers have an associated a coordinate value along the second dimension, and wherein the electronic processor is configured to determine the associated coordinate value along the second dimension for each marker based on a difference between the mean value represented by the marker and a reference value of the CBC parameter for the first lot.

15. The system of claim 14, wherein the reference value of the CBC parameter corresponds to an average of the measured values of the CBC parameter for the first lot.

16. The system of claim 13, wherein the electronic processor is configured to display measured values of the CBC parameter obtained from a plurality of samples from a second lot of a quality control composition, wherein the displaying comprises displaying a second plurality of markers as user-selectable controls corresponding to the measured values from the second lot on the plot,
wherein each marker of the second plurality of markers represents a mean value of corresponding measured values of the CBC parameter for more than one of the samples from the second lot; and
wherein the electronic processor is configured so that when a member of the second plurality of markers is activated, the electronic processor displays the measured values of the CBC parameter for the more than one of the samples of the second lot corresponding to the activated marker.

17. The system of claim 16, wherein the markers corresponding to the samples of the second lot each have an associated coordinate value along the second dimension, and wherein the electronic processor is configured to determine the associated coordinate value along the second dimension for each marker corresponding to the samples of the second lot based on a difference between the marker's designated mean value and a reference value of the CBC parameter for the second lot.

18. The system of claim 17, wherein the reference value of the CBC parameter for the second lot corresponds to an average of the measured values of the CBC parameter for the second lot.

19. The system of claim 13, wherein the electronic processor is configured to display successive markers in a temporal sequence extending parallel to the first dimension and in a direction toward the second dimension on the user interface.

20. The system of claim 19, wherein the electronic processor is configured to display a user-selectable control associated with the first dimension on the user interface, wherein when activated, the user-selectable control allows the user to adjust the direction toward which the temporal sequence of successive markers extends.

21. The system of claim 13, wherein the electronic processor is configured to display on the plot one or more indicators defining a standard range of values for the CBC parameter.

22. The system of claim 21, wherein the electronic processor is configured to:
display members of the plurality of markers that correspond to mean values within the standard range in a first color on the plot; and
display members of the plurality of markers that correspond to mean values outside the standard range in a second color different from the first color on the plot.

23. The system of claim 13, wherein the electronic processor is configured to display on the user interface a user-selectable control for selecting multiple markers, and wherein the electronic processor is configured so that, when multiple markers are selected by activating the user-selectable control for selecting multiple markers, the electronic processor displays statistical information about a distribution of values of the CBC parameter associated with the selected markers on the user interface.

24. The system of claim 13, wherein the electronic processor is configured to determine, at each of a plurality of different measurement times, a mean value of the measured values of the CBC parameter corresponding to the first lot, and to display a marker on the plot that corresponds to the mean value.

* * * * *